US010729793B2

(12) United States Patent
Garrood

(10) Patent No.: US 10,729,793 B2
(45) Date of Patent: Aug. 4, 2020

(54) METHOD FOR IMAGING ARTHRITIS

(71) Applicant: GUY'S AND ST THOMAS' HOSPITAL NHS FOUNDATION TRUST, London, Greater London (GB)

(72) Inventor: Toby Garrood, London (GB)

(73) Assignee: GUY'S AND ST. THOMAS' HOSPITAL NHS FOUNDATION TRUST, Greater London (GB)

( * ) Notice: Subject to any disclaimer, the term of this patent is extended or adjusted under 35 U.S.C. 154(b) by 0 days.

(21) Appl. No.: 15/739,220

(22) PCT Filed: Jun. 23, 2016

(86) PCT No.: PCT/GB2016/051879
§ 371 (c)(1),
(2) Date: Dec. 22, 2017

(87) PCT Pub. No.: WO2016/207636
PCT Pub. Date: Dec. 29, 2016

(65) Prior Publication Data
US 2018/0185523 A1   Jul. 5, 2018

(30) Foreign Application Priority Data

Jun. 23, 2015   (GB) .................................. 1511036.4

(51) Int. Cl.
*A61K 51/08*   (2006.01)
(52) U.S. Cl.
CPC .................................. *A61K 51/082* (2013.01)
(58) Field of Classification Search
CPC ............ A61K 2121/00; A61K 2123/00; A61K 51/00; A61K 51/08; A61K 51/082; A61K 38/00
USPC .......... 424/1.11, 1.65, 1.69, 1.81, 1.85, 1.89, 424/9.1, 9.2, 9.3, 9.4, 9.5, 9.6; 534/7, 534/10–37; 514/1, 1.1; 530/300
See application file for complete search history.

(56) References Cited

U.S. PATENT DOCUMENTS

2006/0029544 A1   2/2006   Sutcliffe-Goulden et al.
2010/0233082 A1*  9/2010   Langstrom ........... A61K 51/088
                                                         424/1.69
2012/0203096 A1   8/2012   Roy et al.

FOREIGN PATENT DOCUMENTS

WO   2005012335 A   2/2005

OTHER PUBLICATIONS

UK Search Report for GB1511036.4, dated May 6, 2016.
International Search Report dated Sep. 8, 2016 for PCT/GB2016/051879.
Wu, Y., et al., "99mTc-3PRGD2 SPECT Imaging, of angiogenesis of rheumatoid arthritis in rats and humans", Journal of Nuclear Medicine, vol. 56, No. supplement 3, May 1, 2015.
Jia, B., et al., Blood Clearance Kinetics, Biodistribution, and Radiation Dosimetry of a Kit-Formulated Integrin av(B3-Selective Radiotracer 99m Tc-3PRGD2 in Non-Human Primates, Molecular Imaging and Biology (2011)13:730-736.
Terry, S., et al., Monitoring therapy response in rheumatoid arthritis: a multiprobe approach. Journal of Nuclear Medicine, vol. 56, No. supplement 3, May 1, 2015 and Terry, S., et al., Can In-RGD2 Monitor Response to Therapy in Head and Neck Tumor Xenografts?, The Journal of Nuclear Medicine, vol. 55, No. 11, Oct. 27, 2014.
Wirrwar, A, et al., "Dynamic imaging of arthritic inflammation in mouse-models using high-resolution multi-pinhole spect and in-111 labelled cyclic RGD peptide", Annals of the Rheumatic Diseases, vol. 66, No. Suppl. 2, Jul. 2007.
Vanhagen, P. M., et al., "Somatostatin receptor imaging. The presence of somatostatin receptors in rheumatoid arthritis", Arthritis & Rheumatism, vol. 37, No. 10, Oct. 1, 1994.
Caveliers, V., et al., "Evaluation of 99mTc-RP128 as a potential inflammation imaging agent: Human dosimetry and first clinical results", The Journal of Nuclear Medicine, Society of Nuclear Medicine, US, vol. 42, No. 1, Jan. 1, 2001.
Edwards, D., et al., "Tc-NC100692—a tracer for imaging vitronectin receptors associated with angiogenesis: a preclinical investigation", Nuclear Medicine and Biology, Elsevier, NY, US, vol. 35, No. 3, Mar. 17, 2008.
Axelsson, R., et al., "An open-label, multicenter, phase 2a study to assess the feasibility of imaging metastases in late-stage cancer patients with the alpha v beta 3-selective angiogenesis imaging agent 99mTc-NC100692", ACTA Radiologica (Stockholm, Sweden : 1987) Feb. 2010, vol. 51, No. I, Feb. 2010.
Garrood, T., et al., "Whole-Body Synovial Uptake of a 99mtc-Labelled RGD Peptide is Highly Correlated with Power Doppler Ultrasound", Arthritis Rheumatol., vol. 67 (suppl 10), Sep. 29, 2015.

* cited by examiner

*Primary Examiner* — D. L. Jones

(74) *Attorney, Agent, or Firm* — King & Schickli, PLLC

(57) ABSTRACT

The invention relates to a method of imaging arthritis in a subject, comprising administering to the subject a tracer which comprises a peptide conjugated to a radionuclide, and imaging the subject by 2D nuclear imaging or by 3D detection of single-photon emission events.

7 Claims, 5 Drawing Sheets

HANDS & FEET STATICS 120min

METHOD FOR IMAGING ARTHRITIS

This application is the national stage of international patent application no. PCT/GB2016/051879 filed on Jun. 23, 2016 which in turn claims priority from 1511036.4 (GB) filed on Jun. 23, 2015, the disclosures of which are incorporated herein by reference in their entirety.

TECHNICAL FIELD

The invention relates to a method of imaging arthritis.

BACKGROUND

Rheumatoid arthritis (RA) is an inflammatory joint disease which, untreated, results in progressive joint damage and disability.[1] Early aggressive treatment offers the best chances of achieving good long-term outcomes in RA, but it remains a challenge to optimise early and accurate diagnosis of patients requiring such treatment.

The inflamed synovial membrane in RA has abundant new vessel formation; this is an early event and it has been shown to correlate with the clinical degree of synovitis.[7,8] Furthermore, many of these vessels are immature, indicating a high degree of turnover which is likely to be contribute to increased vascular permeability.[9] The integrin $\alpha_v\beta_3$ is expressed at low levels in health, but is up-regulated on activated vascular endothelial cells in angiogenesis as well as on activated macrophages and osteoclasts,[10,11] both of which accumulate in the inflamed joint.[12,13] Expression of $\alpha_v\beta_3$ is markedly upregulated on synovial vascular endothelial cells in both seropositive and seronegative arthritis.[14,15]

Over the last decade high-resolution ultrasound (US) of joints, particularly when combined with power Doppler (PDUS) assessment, has been increasingly employed in the assessment of inflammatory arthritis. Evidence of inflammatory activity can be seen in clinically uninflamed joints,[2] indicating that US has superior sensitivity to clinical examination. Furthermore, the presence of active synovial inflammation as determined by power Doppler signal has been shown to be predictive of joint damage.[3,4] PDUS images vascular activity in the synovium and has been shown to correlate with histologically determined synovial vascularity[5] and inflammation.[6]

There is a substantial body of evidence that vascular imaging is a valuable predictive tool in RA for persistence of inflammation and for joint damage. PDUS has been used as a surrogate for vascular imaging, but the technique is limited in terms of its accessibility. Despite its advantages, US is available in only a relatively small number of rheumatology departments. It is time-consuming and therefore in daily practice assessment is limited to a few joints; thus comprehensive imaging of all joints is impractical in routine clinical practice. Furthermore, US is expensive in terms of resources and the number of rheumatologists with the requisite skills remains limited. A practical alternative method to US for imaging arthritis is thus needed.

Magnetic Resonance Imaging (MRI) has a similar sensitivity to US for joint inflammation. However, using MRI it is impractical to image more than a few joints at a time. MRI is also extremely expensive. MRI therefore has a limited role in the routine assessment of inflammatory arthritis, and is not a viable alternative to US in most cases.

Positron emission tomography (PET) has been suggested as an alternative approach for imaging arthritis. For example, a recent study demonstrated some specificity of uptake of a $^{68}$Ga-labeled dimeric RGD peptide for PET imaging in RA.[22] However, the study demonstrated limited correlation between the results of the PET imaging and clinical assessment. Furthermore, PET imaging does not have potential for routine clinical practice due to the high cost and restricted accessibility of PET equipment. PET is thus not a practical alternative to US or MRI for imaging RA.

Various tracers have been investigated for use in nuclear imaging, and both $^{99m}$Tc- and $^{18}$F-labelled compounds are being validated for the imaging of neoangiogenesis in cancers.[19-21] However, to date, a suitable method of imaging arthritis by nuclear imaging has not been demonstrated. A practical alternative method to (PD)US, MRI and PET for imaging arthritis is thus needed.

SUMMARY

The inventors have developed a new method of imaging arthritis in a subject. Specifically, the inventors have found that a tracer comprising a peptide conjugated to a radionuclide can be used very effectively to image arthritis in a subject by 2D nuclear imaging or by 3D detection of single-photon emission events.

The methods of the invention overcome many of the problems associated with (PD)US, MRI and PET. Specifically, the methods of the invention have the potential to allow rapid and cost-effective imaging of synovial inflammation at the whole-body level. The use, as described herein, of tracers which comprise a peptide conjugated to a radionuclide offers advantages in terms of specificity for neoangiogenic vessels within the synovial tissue and of potential retention in the inflamed joint by binding to activated macrophages and osteoclasts. Further, the inventors have unexpectedly found an excellent correlation between the new nuclear imaging methods and existing gold-standard ultrasound techniques (see, for example, FIGS. 4 and 5). The methods of the invention thus allow particularly sensitive and specific imaging of inflamed joints. Such imaging has potential to be valuable not only in diagnosis but also in having a critical influence on treatment decisions in patients with established RA, specifically in optimising the use of expensive biologic agents in patients with high disease activity and those in remission.

Accordingly, in one aspect the invention provides a method of imaging arthritis in a subject, comprising administering to the subject a tracer which comprises a peptide conjugated to a radionuclide, and imaging the subject by 2D nuclear imaging or by 3D detection of single-photon emission events. Usually, imaging the subject comprises imaging the subject by 2D scintigraphy using a gamma camera or by single photon emission computational tomography (SPECT). Typically, the arthritis is inflammatory arthritis. Generally, the radionuclide emits gamma radiation. Often, the peptide comprises a R-G-D moiety as described herein.

In another aspect, the invention provides use of a tracer which comprises a peptide conjugated to a radionuclide as an imaging agent for imaging arthritis by 2D nuclear imaging or by 3D detection of single-photon emission events. Typically, the tracer, imaging agent, arthritis and subject are as further described herein.

The methods of the invention find utility in medical diagnosis. Therefore, the invention provides a method of diagnosing arthritis in a subject, which method comprises (a) administering to the subject a tracer which comprises a peptide conjugated to a radionuclide; (b) imaging the subject by 2D nuclear imaging or by 3D detection of single-photon emission events; and (c) determining whether or not the subject has arthritis. Usually, the tracer, imaging agent, arthritis and subject are as further described herein.

The invention also provides a tracer for use in the diagnosis of arthritis in a subject, wherein the tracer comprises a peptide conjugated to a radionuclide; and wherein the diagnosis comprises (a) administering the tracer to the subject; (b) imaging the subject by 2D nuclear imaging or by 3D detection of single-photon emission events; and (c) determining whether or not the subject has arthritis. Often, the tracer, imaging agent, arthritis and subject are as further described herein.

The invention also provides a method of evaluating the activity of a pharmaceutical for the treatment of arthritis, comprising
    administering a tracer to a subject, wherein the tracer comprises a peptide conjugated to a radionuclide, and wherein the subject has arthritis;
    detecting the tracer by imaging the subject by 2D nuclear imaging or by 3D detection of single-photon emission events;
    administering the pharmaceutical to the subject;
    detecting the tracer by imaging the subject by 2D nuclear imaging or by 3D detection of single-photon emission events after administering the pharmaceutical to the subject; and
    evaluating changes in the image of the subject or the detected amount of the tracer before and after administration of the pharmaceutical.

Usually, the tracer, imaging agent, arthritis and subject are as further described herein.

BRIEF DESCRIPTION OF THE DRAWING FIGURES

FIG. 1 shows representative whole body scans of 2 patients at 180 minutes. Uptake can be seen in the hands, wrist, knees, ankles and feet. In addition, uptake is seen in the shoulders and elbows in the first upper images.

DETAILED DESCRIPTION

Definitions

Figure 1:
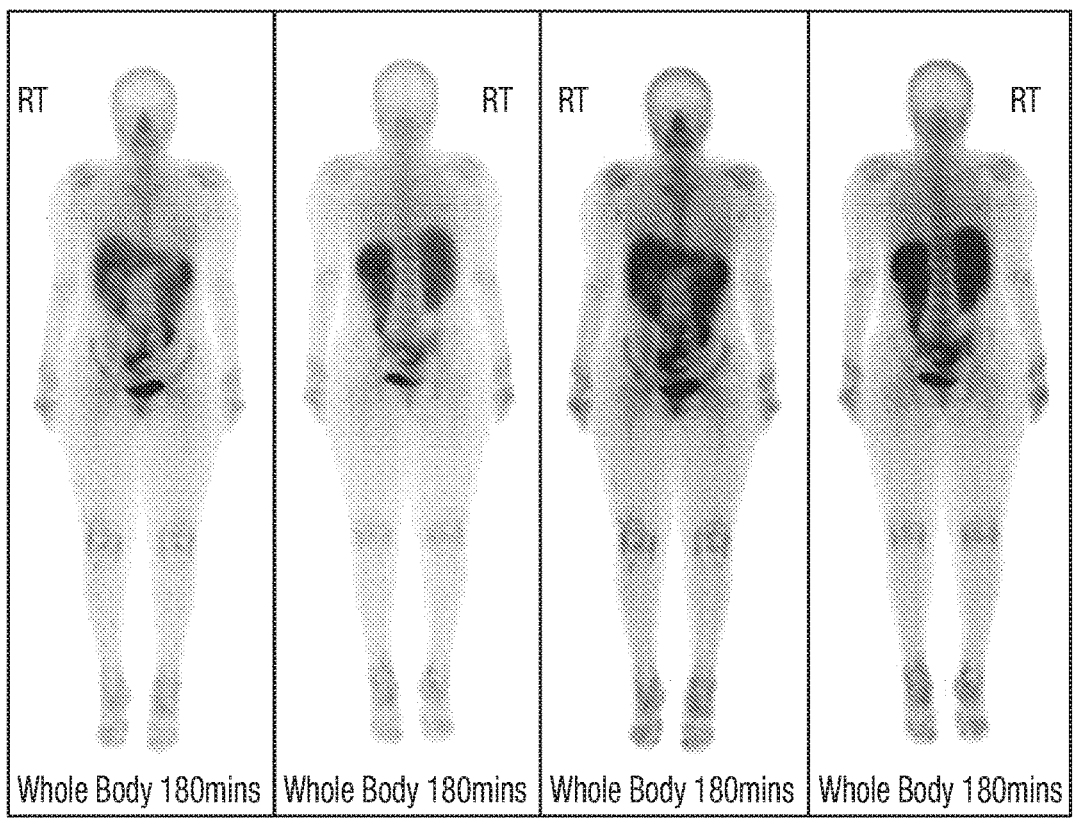
Figure 1:
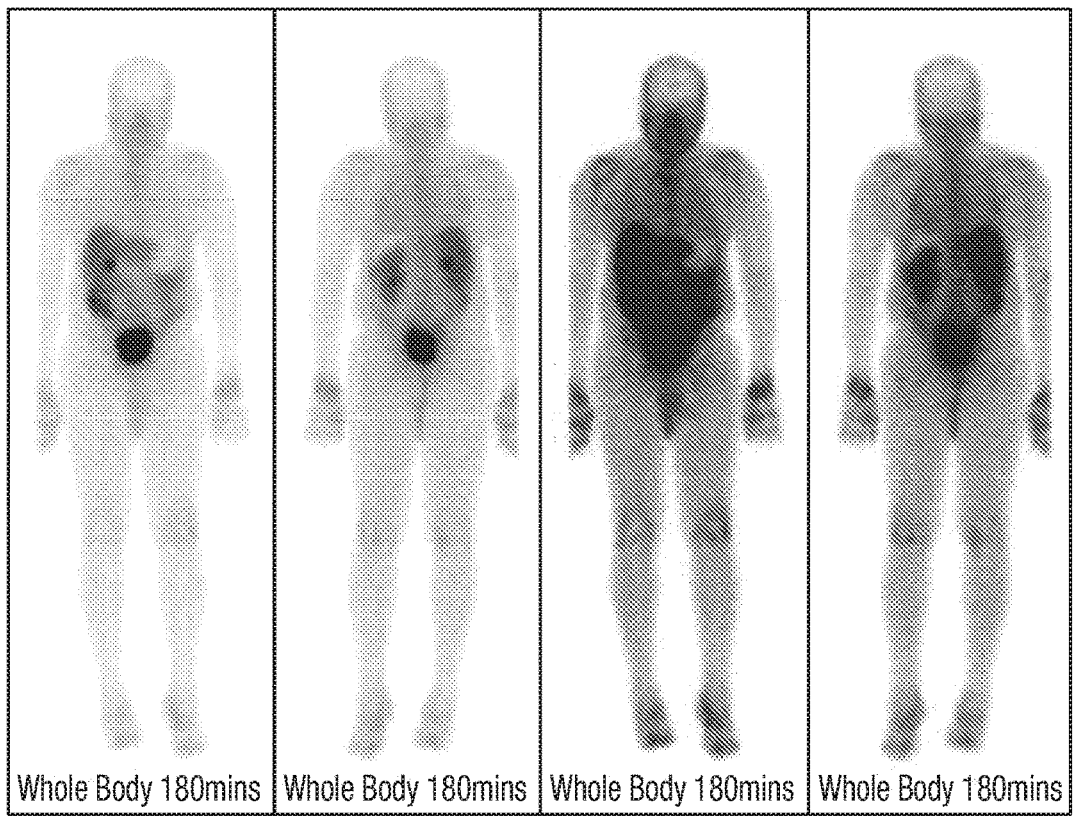

The following substituent definitions apply with respect to the compounds defined herein:

A $C_1$ to $C_{10}$ alkyl group is an unsubstituted or substituted, straight or branched chain saturated hydrocarbon radical. Typically it is $C_1$ to $C_6$ alkyl, for example methyl, ethyl, propyl, butyl, pentyl or hexyl, or $C_1$ to $C_4$ alkyl, for example methyl, ethyl, i-propyl, n-propyl, t-butyl, s-butyl or n-butyl, for example $C_1$ to $C_2$ alkyl, e.g. methyl or ethyl, typically methyl. When an alkyl group is substituted it typically bears one or more substituents selected from substituted or unsubstituted $C_1$ to $C_{10}$ alkyl, substituted or unsubstituted aryl (as defined herein), cyano, amino, $C_1$ to $C_{10}$ alkylamino, di($C_1$ to $C_{10}$)alkylamino, arylamino, diarylamino, arylalkylamino, amido, acylamido, hydroxy, oxo, halo, carboxy, ester, acyl, acyloxy, $C_1$ to $C_{10}$ alkoxy, aryloxy, haloalkyl, sulfonic acid, sulthydryl (i.e. thiol, —SH), $C_1$ to $C_{10}$ alkylthio, arylthio, sulfonyl, phosphoric acid, phosphate ester, phosphonic acid and phosphonate ester. Examples of substituted alkyl groups include haloalkyl, hydroxyalkyl, aminoalkyl, alkoxyalkyl and alkaryl groups. The term alkaryl, as used herein, pertains to a $C_1$ to $C_{10}$ alkyl group in which at least one hydrogen atom has been replaced with an aryl group. Examples of such groups include, but are not limited to, benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—), cinnamyl (Ph-CH=CH—CH$_2$—). Typically a substituted $C_1$ to $C_{10}$ alkyl group carries 1, 2 or 3 substituents, for instance 1 or 2.

A $C_2$ to $C_{10}$ alkenyl group is an unsubstituted or substituted, straight or branched chain unsaturated hydrocarbon radical having one or more, e.g. one or two, double bonds. Typically it is $C_2$ to $C_6$ alkenyl, for example ethenyl, propenyl, butenyl, pentenyl or hexenyl, or $C_2$ to $C_4$ alkenyl, for example ethenyl, i-propenyl, n-propenyl, t-butenyl, s-butenyl or n-butenyl. When an alkenyl group is substituted it typically bears one or more substituents selected from substituted or unsubstituted $C_1$ to $C_{10}$ alkyl, substituted or unsubstituted aryl (as defined herein), cyano, amino, $C_1$ to $C_{10}$ alkylamino, di($C_1$ to $C_{10}$)alkylamino, arylamino, diarylamino, arylalkylamino, amido, acylamido, hydroxy, oxo, halo, carboxy, ester, acyl, acyloxy, $C_1$ to $C_{10}$ alkoxy, aryloxy, haloalkyl, sulfonic acid, sulthydryl (i.e. thiol, —SH), $C_1$ to $C_{10}$ alkylthio, arylthio, sulfonyl, phosphoric acid, phosphate ester, phosphonic acid and phosphonate ester. Examples of substituted alkenyl groups include haloalkenyl, hydroxyalkenyl, aminoalkenyl, alkoxyalkenyl and alkenaryl groups. The term alkenaryl, as used herein, pertains to a $C_2$ to $C_{10}$ alkenyl group in which at least one hydrogen atom has been replaced with an aryl group. Examples of such groups include, but are not limited to, styryl (PhCH=CH—), Ph$_2$C=CH—, PhCH=C(Ph)-, and cinnamyl (Ph-CH=CH—CH$_2$—). Typically a substituted $C_2$ to $C_{10}$ alkenyl group carries 1, 2 or 3 substituents, for instance 1 or 2.

A $C_3$ to $C_{10}$ cycloalkyl group is an unsubstituted or substituted alkyl group which is also a cyclyl group; that is, a monovalent moiety obtained by removing a hydrogen atom from an alicyclic ring atom of a carbocyclic ring of a carbocyclic compound, which moiety has from 3 to 10 carbon atoms (unless otherwise specified), including from 3 to 10 ring atoms. Thus, the term "cycloalkyl" includes the sub-classes cycloalkyenyl and cycloalkynyl. Examples of groups of $C_3$ to $C_{10}$ cycloalkyl groups include $C_3$ to $C_7$ cycloalkyl, e.g. $C_5$ or $C_6$ cycloalkyl. When a $C_3$ to $C_{10}$ cycloalkyl group is substituted it typically bears one or more substituents selected from $C_1$ to $C_6$ alkyl which is unsubstituted, aryl (as defined herein), cyano, amino, $C_1$ to $C_{10}$ alkylamino, di($C_1$ to $C_{10}$)alkylamino, arylamino, diarylamino, arylalkylamino, amido, acylamido, hydroxy, oxo, halo, carboxy, ester, acyl, acyloxy, $C_1$ to $C_{20}$ alkoxy, aryloxy, haloalkyl, sulfonic acid, sulthydryl (i.e. thiol, —SH), $C_1$ to $C_{10}$ alkylthio, arylthio, phosphoric acid, phosphate ester, phosphonic acid and phosphonate ester and sulfonyl. Typically a substituted $C_3$ to $C_{10}$ cycloalkyl group carries 1, 2 or 3 substituents, for instance 1 or 2.

Examples of $C_3$ to $C_{10}$ cycloalkyl groups include, but are not limited to, those derived from saturated monocyclic hydrocarbon compounds, which $C_3$ to $C_{10}$ cycloalkyl groups are unsubstituted or substituted as defined above: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds: camphene ($C_{10}$), limonene ($C_{10}$), pinene ($C_{10}$), polycyclic hydrocarbon compounds having an aromatic ring: indene ($C_9$), indane (e.g., 2,3-dihydro-1H-indene) ($C_9$), tetraline (1,2,3,4-tetrahydronaphthalene) ($C_{10}$).

A $C_3$ to $C_{10}$ heterocyclyl group is an unsubstituted or substituted monovalent moiety obtained by removing a hydrogen atom from a ring atom of a heterocyclic compound, which moiety has from 3 to 10 ring atoms (unless otherwise specified), of which from 1 to 5 are ring heteroatoms. Preferably, each ring has from 3 to 7 ring atoms, of which from 1 to 4 are ring heteroatoms. Often, each ring has from 5 to 6 ring atoms, of which from 1 to 2 are ring heteroatoms. When a $C_3$ to $C_{10}$ heterocyclyl group is substituted it typically bears one or more substituents selected from $C_1$ to $C_6$ alkyl which is unsubstituted, aryl (as defined herein), cyano, amino, $C_1$ to $C_{10}$ alkylamino, di($C_1$ to $C_{10}$) alkylamino, arylamino, diarylamino, arylalkylamino, amido, acylamido, hydroxy, oxo, halo, carboxy, ester, acyl, acyloxy, $C_1$ to $C_{20}$ alkoxy, aryloxy, haloalkyl, sulfonic acid, sulthydryl (i.e. thiol, —SH), $C_1$ to $C_{10}$ alkylthio, arylthio, phosphoric acid, phosphate ester, phosphonic acid and phosphonate ester and sulfonyl. Typically a substituted $C_3$ to $C_{10}$ heterocyclyl group carries 1, 2 or 3 substituents, for instance 1 or 2.

Examples of groups of heterocyclyl groups include $C_5$ to $C_{10}$ heterocyclyl, $C_3$ to $C_7$ heterocyclyl, $C_5$ to $C_7$ heterocyclyl, and $C_5$ to $C_6$ heterocyclyl.

Examples of (non-aromatic) monocyclic $C_3$ to $C_{10}$ heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of $C_3$ to $C_{10}$ heterocyclyl groups which are also aryl groups are described below as heteroaryl groups.

An aryl group is a substituted or unsubstituted, monocyclic or fused polycyclic aromatic group which typically contains from 6 to 14 carbon atoms, preferably from 6 to 10 carbon atoms, e.g. 6 carbon atoms, in the ring portion. Examples include phenyl (i.e. monocyclic), naphthyl, indenyl and indanyl (i.e. fused bicyclic), anthracenyl (i.e. fused tricyclic), and pyrenyl (i.e. fused tetracyclic) groups. An aryl group is unsubstituted or substituted. When an aryl group as defined above is substituted it typically bears one or more substituents selected from $C_1$ to $C_6$ alkyl which is unsubstituted (to form an aralkyl group), aryl which is unsubstituted, cyano, amino, $C_1$ to $C_{10}$ alkylamino, di($C_1$ to $C_{10}$)alkylamino, arylamino, diarylamino, arylalkylamino, amido, acylamido, hydroxy, halo, carboxy, ester, acyl, acyloxy, $C_1$ to $C_{20}$ alkoxy, aryloxy, haloalkyl, sulthydryl (i.e. thiol, —SH), $C_1$ to $C_{10}$ alkylthio, arylthio, sulfonic acid, phosphoric acid, phosphate ester, phosphonic acid and phosphonate ester and sulfonyl. Typically it carries 0, 1, 2 or 3 substituents. A substituted aryl group may be substituted in two positions with a single $C_1$ to $C_6$ alkylene group, or with a bidentate group represented by the formula —X—$C_1$ to $C_6$ alkylene, or —X—$C_1$ to $C_6$ alkylene-X—, wherein X is selected from O, S and NR, and wherein R is H, aryl or $C_1$ to $C_6$ alkyl. Thus a substituted aryl group may be an aryl group fused with a cycloalkyl group or with a heterocyclyl group. The term aralkyl as used herein, pertains to an aryl group in which at least one hydrogen atom (e.g., 1, 2, 3) has been substituted with a $C_1$ to $C_6$ alkyl group. Examples of such groups include, but are not limited to, tolyl (from toluene), xylyl (from xylene), mesityl (from mesitylene), and cumenyl (or cumyl, from cumene), and duryl (from durene).

As used herein, a heteroaryl group is a substituted or unsubstituted monocyclic or fused polycyclic (e.g. bicyclic or tricyclic) aromatic group which typically contains from 5 to 14 atoms in the ring portion including at least one heteroatom, for example 1, 2 or 3 heteroatoms, selected from O, S, N, P, Se and Si, more typically from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, thiazolyl, imidazolyl, triazolyl, pyrazolyl, oxazolyl, isothiazolyl, benzofuranyl, isobenzofuranyl, benzothiophenyl, indolyl, indazolyl, carbazolyl, acridinyl, purinyl, cinnolinyl, quinoxalinyl, naphthyridinyl, benzimidazolyl, benzoxazolyl, quinolinyl, quinazolinyl and isoquinolinyl. A heteroaryl group is often a 5- or 6-membered ring. However, as used herein, references to a heteroaryl group also include fused polycyclic ring systems, including for instance fused bicyclic systems in which a heteroaryl group is fused to an aryl group. When the heteroaryl group is such a fused heteroaryl group, preferred examples are fused ring systems wherein a 5- to 6-membered heteroaryl group is fused to a phenyl group. Examples of such fused ring systems are benzofuranyl, isobenzofuranyl, benzothiophenyl, indolyl, indazolyl, benzimidazolyl, benzoxazolyl, quinolinyl, quinazolinyl and isoquinolinyl moieties.

A heteroaryl group may be unsubstituted or substituted, for instance, as specified above for aryl. Typically it carries 0, 1, 2 or 3 substituents.

A $C_1$ to $C_{10}$ alkylene group is an unsubstituted or substituted bidentate moiety obtained by removing two hydrogen atoms, either both from the same carbon atom, or one from each of two different carbon atoms, of a hydrocarbon compound having from 1 to 10 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below. Usually, however, it is a saturated aliphatic (non-cyclic) group. Typically it is $C_1$ to $C_6$ alkylene, or $C_1$ to $C_4$ alkylene, for example methylene, ethylene, i-propylene, n-propylene, t-butylene, s-butylene or n-butylene. It may for instance be $C_2$ to $C_4$ alkylene. Or, for instance, it may be $C_1$ to $C_3$ alkylene, for example methylene, ethylene, n-propylene or i-propylene. (Although usually, herein, a $C_1$ to $C_3$ alkylene refers to methylene, ethylene or n-proylene.) It may also be pentylene, hexylene, heptylene, octylene and the various branched chain isomers thereof. An alkylene group may be unsubstituted or substituted, for instance, as specified above for alkyl. Typically a substituted alkylene group carries 1, 2 or 3 substituents, for instance 1 or 2.

In this context, the prefixes (e.g., $C_1$ to $C_4$, $C_1$ to $C_6$, $C_1$ to $C_7$, $C_1$ to $C_{10}$, $C_2$ to $C_7$, $C_3$ to $C_7$, etc.) denote the number of carbon atoms, or range of number of carbon atoms. For example, the term "$C_1$ to $C_4$ alkylene," as used herein, pertains to an alkylene group having from 1 to 4 carbon atoms. Examples of groups of alkylene groups include $C_1$ to $C_4$ alkylene ("lower alkylene"), $C_1$ to $C_7$ alkylene, and $C_1$ to $C_{10}$ alkylene.

Examples of linear saturated $C_1$ to $C_7$ alkylene groups include, but are not limited to, —$(CH_2)_n$— where n is an integer from 1 to 7, for example, —$CH_2$— (methylene), —$CH_2CH_2$— (ethylene), —$CH_2CH_2CH_2$— (propylene), and —$CH_2CH_2CH_2CH_2$— (butylene).

Examples of branched saturated $C_1$ to $C_7$ alkylene groups include, but are not limited to, —$CH(CH_3)$—, —$CH(CH_3)$ $CH_2$—, —$CH(CH_3)CH_2CH_2$—, —$CH(CH_3)$ $CH_2CH_2CH_2$—, —$CH_2CH(CH_3)CH_2$—, —$CH_2CH(CH_3)$ $CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_1$ to $C_7$ alkylene groups include, but is not limited to, —CH=CH— (vinylene), —CH=CH—$CH_2$—, —$CH_2$—CH=$CH_2$—, —CH=CH—$CH_2$—$CH_2$—, —CH=CH—$CH_2$—$CH_2$ $CH_2$—, —CH=CH—CH=CH—, —CH=CH— CH=CH—$CH_2$—, —CH=CH—$CH_2$—CH=CH—$CH_2$ $CH_2$—, —CH=CH—$CH_2$—CH=CH—, and —CH=CH—$CH_2$—$CH_2$—CH=CH—.

Examples of branched partially unsaturated $C_1$ to $C_7$ alkylene groups include, but are not limited to, —C($CH_3$) =CH—, —C($CH_3$)=CH—$CH_2$—, and —CH=CH—CH ($CH_3$)—.

Examples of alicyclic saturated $C_1$ to $C_7$ alkylene groups include, but are not limited to, cyclopentylene (e.g., cyclopent-1,3-ylene), and cyclohexylene (e.g., cyclohex-1,4-ylene).

Examples of alicyclic partially unsaturated $C_1$ to $C_7$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

$C_1$ to $C_{10}$ alkylene and $C_1$ to $C_{10}$ alkyl groups as defined herein are either uninterrupted or interrupted by one or more heteroatoms or heterogroups, such as S, O or N(R") wherein R" is H, $C_1$ to $C_6$ alkyl, $C_2$ to $C_6$ alkenyl, $C_2$ to $C_6$ alkynyl, aryl (typically phenyl), or heteroaryl, or by one or more arylene or heteroarylene groups, typically $C_6$ to $C_{10}$ arylene or $C_5$ to $C_{10}$ heteroarylene, (typically arylene, more typically phenylene) groups, or by one or more —C(O)—, —C(O) O—, —C(O)N(R")— or —N(R")C(O)— groups. The phrase "optionally interrupted" as used herein thus refers to a $C_1$ to $C_{10}$ alkyl group or an alkylene group, as defined above, which is uninterrupted or which is interrupted between adjacent carbon atoms by a heteroatom such as oxygen or sulfur, by a heterogroup such as N(R") wherein R" is H, aryl, heteroaryl or $C_1$ to $C_6$ alkyl, or by an arylene or heteroarylene (typically arylene, more typically phenylene) group, or by a —C(O)—, —C(O)O— or —C(O)N (R")— group, again wherein R" is H, aryl or $C_1$ to $C_6$ alkyl.

For instance, a $C_1$ to $C_{10}$ alkyl group such as n-butyl may be interrupted by the heterogroup N(R") as follows: —$CH_2$N(R")$CH_2CH_2CH_3$, —$CH_2CH_2$N(R")$CH_2CH_3$, or —$CH_2CH_2CH_2$N(R")$CH_3$. Similarly, an alkylene group such as n-butylene may be interrupted by the heterogroup N(R") as follows: —$CH_2$N(R")$CH_2CH_2CH_2$—, —$CH_2CH_2$N(R")$CH_2CH_2$—, or —$CH_2CH_2CH_2$N(R") $CH_2$—. Typically an interrupted group, for instance an interrupted $C_1$ to $C_{10}$ alkylene or $C_1$ to $C_{10}$ alkyl group, is interrupted by 1, 2 or 3 heteroatoms or heterogroups or by 1, 2 or 3 arylene (typically phenylene) groups. More typically, an interrupted group, for instance an interrupted $C_1$ to $C_{10}$ alkylene or $C_1$ to $C_{10}$ alkyl group, is interrupted by 1 or 2 heteroatoms or heterogroups or by 1 or 2 arylene (typically phenylene) groups. For instance, a $C_1$ to $C_{20}$ alkyl group such as n-butyl may be interrupted by 2 heterogroups N(R") as follows: —$CH_2$N(R")$CH_2$N(R")$CH_2CH_3$.

A $C_2$ to $C_{10}$ alkenylene group is an unsubstituted or substituted bidentate moiety obtained by removing two hydrogen atoms, either both from the same carbon atom, or one from each of two different carbon atoms, of a hydrocarbon compound having from 2 to 10 carbon atoms (unless otherwise specified), which may be aliphatic or alicyclic, and which is partially unsaturated, or fully unsaturated. Usually an alkenylene group is obtained by removing two hydrogen atoms from an alkenyl group as defined herein. Typically, an alkenylene group is an unsaturated aliphatic (non-cyclic) group. Typically it is $C_2$ to $C_6$ alkenylene, or $C_2$ to $C_4$ alkenylene, for example ethenylene, i-propenylene, n-propenylene, t-butenylene, s-butenylene or n-butenylene. It may for instance be $C_2$ or $C_3$ alkenylene, for example ethenylene, n-propenylene or i-propenylene, often ethenylene. An $C_2$ to $C_{10}$ alkenylene group may also be pentenylene, hexenylene, heptenylene, octenylene and the various branched chain isomers thereof An alkenylene group may be unsubstituted or substituted, for instance, as specified above for alkenyl. Typically a substituted alkenylene group carries 1, 2 or 3 substituents, for instance 1 or 2.

A $C_3$ to $C_{10}$ cycloalkylene group is an unsubstituted or substituted bidentate moiety obtained by removing two hydrogen atoms, either both from the same carbon atom, or one from each of two different carbon atoms, of a cyclic hydrocarbon compound having from 3 to 10 carbon atoms (unless otherwise specified), and which is saturated or partially unsaturated. Usually an cycloalkylene group is obtained by removing two hydrogen atoms from an cycloalkyl group as defined herein. Typically, a cycloalkylene group is $C_5$ to $C_8$ alkenylene, e.g. $C_5$ to $C_7$ cycloalkylene such as $C_5$ or $C_6$ cycloalkylene. Most often a cycloalkylene group is cyclopentylene or cyclohexylene. A cycloalkylene group may be unsubstituted or substituted, for instance, as specified above for cycloalkyl. Typically a substituted cycloalkylene group carries 1, 2 or 3 substituents, for instance 1 or 2.

A $C_3$ to $C_{10}$ heterocyclylene group is an unsubstituted or substituted bidentate moiety obtained by removing two hydrogen atoms, either both from the same ring atom, or one from each of two different ring atoms, of a heterocyclic compound having from 3 to 10 ring atoms (unless otherwise specified), and which is saturated or partially unsaturated. Usually an heterocyclylene group is obtained by removing two hydrogen atoms from an heterocyclyl group as defined herein. Typically, a heterocyclylene group is $C_5$ to $C_8$ heterocyclylene, e.g. $C_5$ to $C_7$ heterocyclylene such as $C_5$ or $C_6$ heterocyclylene. Most often a heterocyclylene group is pyridinylene, pyrimidinylene, pyrrolidinylene. A heterocyclylene group may be unsubstituted or substituted, for instance, as specified above for heterocycly. Typically a substituted heterocyclylene group carries 1, 2 or 3 substituents, for instance 1 or 2.

An arylene group is an unsubstituted or substituted monocyclic or fused polycyclic bidentate moiety obtained by removing two hydrogen atoms, one from each of two different aromatic ring atoms of an aromatic compound, which moiety has from 5 to 14 ring atoms (unless otherwise specified). Typically, each ring has from 5 to 7 or from 5 to 6 ring atoms. An arylene group may be unsubstituted or substituted, for instance, as specified above for aryl.

In this context, the prefixes (e.g., $C_5$ to $C_{20}$, $C_6$ to $C_{20}$, $C_5$ to $C_{14}$, $C_5$ to $C_7$, $C_5$ to $C_6$, etc.) denote the number of ring atoms, or range of number of ring atoms, whether carbon atoms or heteroatoms. For example, the term "$C_5$ to $C_6$ arylene," as used herein, pertains to an arylene group having 5 or 6 ring atoms. Examples of groups of arylene groups include $C_5$ to $C_{20}$ arylene, $C_6$ to $C_{20}$ arylene, $C_5$ to $C_{14}$ arylene, $C_6$ to $C_{14}$ arylene, $C_6$ to $C_{10}$ arylene, $C_5$ to $C_{12}$ arylene, $C_5$ to $C_{10}$ arylene, $C_5$ to $C_7$ arylene, $C_5$ to $C_6$ arylene, $C_5$ arylene, and $C_6$ arylene.

The ring atoms may be all carbon atoms, as in "carboarylene groups" (e.g., $C_6$ to $C_{20}$ carboarylene, $C_6$ to $C_{14}$ carboarylene or $C_6$ to $C_{10}$ carboarylene).

Examples of $C_6$ to $C_{20}$ arylene groups which do not have ring heteroatoms (i.e., $C_6$ to $C_{20}$ carboarylene groups) include, but are not limited to, those derived from the compounds discussed above in regard to aryl groups, e.g. phenylene, and also include those derived from aryl groups which are bonded together, e.g. phenylene-phenylene (diphenylene) and phenylene-phenylene-phenylene (triphenylene).

Alternatively, the ring atoms may include one or more heteroatoms, as in "heteroarylene groups" (e.g., $C_5$ to $C_{14}$ heteroarylene). A heteroarylene group is an unsubstituted or substituted monocyclic or fused polycyclic bidentate moiety obtained by removing two hydrogen atoms, one from each of two different aromatic ring atoms of an heteroaromatic compound, which moiety has from 5 to 14 ring atoms (unless otherwise specified). Typically, each ring has from 5 to 7 or from 5 to 6 ring atoms. An heteroarylene group may be unsubstituted or substituted, for instance, as specified above for heteroaryl. Examples of $C_5$ to $C_{14}$ heteroarylene groups include, but are not limited to, those derived from the compounds discussed above in regard to heteroaryl groups.

As used herein the term oxo represents a group of formula: =O

As used herein the term acyl represents a group of formula: —C(=O)R, wherein R is an acyl substituent, for example, a substituted or unsubstituted $C_1$ to $C_{20}$ alkyl group, a $C_1$ to $C_{20}$ perfluoroalkyl group, a substituted or unsubstituted $C_3$ to $C_{10}$ cycloalkyl group, a substituted or unsubstituted $C_3$ to $C_{10}$ heterocyclyl group, a substituted or unsubstituted aryl group, a perfluoroaryl group, or a substituted or unsubstituted heteroaryl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

As used herein the term acyloxy (or reverse ester) represents a group of formula: —OC(=O)R, wherein R is an acyloxy substituent, for example, substituted or unsubstituted $C_1$ to $C_{10}$ alkyl group, a substituted or unsubstituted $C_3$ to $C_{10}$ heterocyclyl group, or a substituted or unsubstituted aryl group, typically a $C_1$ to $C_6$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

As used herein the term ester (or carboxylate, carboxylic acid ester or oxycarbonyl) represents a group of formula: —C(=O)OR, wherein R is an ester substituent, for example, a substituted or unsubstituted $C_1$ to $C_{10}$ alkyl group, a substituted or unsubstituted $C_3$ to $C_{20}$ heterocyclyl group, or a substituted or unsubstituted aryl group (typically a phenyl group). Examples of ester groups include, but are not limited to, —C(=O)OCH$_3$, —C(=O)OCH$_2$CH$_3$, —C(=O)OC(CH$_3$)$_3$, and —C(=O)OPh.

As used herein the term amino represents a group of formula —NH$_2$. The term $C_1$ to $C_{10}$ alkylamino represents a group of formula —NHR' wherein R' is a $C_1$ to $C_{10}$ alkyl group, preferably a $C_1$ to $C_6$ alkyl group, as defined previously. The term di($C_1$ to $C_{10}$)alkylamino represents a group of formula —NR'R" wherein R' and R" are the same or different and represent $C_1$ to $C_{10}$ alkyl groups, preferably $C_1$ to $C_6$ alkyl groups, as defined previously. The term arylamino represents a group of formula —NHR' wherein R' is an aryl group, preferably a phenyl group, as defined previously. The term diarylamino represents a group of formula —NR'R" wherein R' and R" are the same or different and represent aryl groups, preferably phenyl groups, as defined previously. The term arylalkylamino represents a group of formula —NR'R" wherein R' is a $C_1$ to $C_{10}$ alkyl group, preferably a $C_1$ to $C_6$ alkyl group, and R" is an aryl group, preferably a phenyl group.

A halo group is chlorine, fluorine, bromine or iodine (a chloro group, a fluoro group, a bromo group or an iodo group). It is typically chlorine, fluorine or bromine.

As used herein the term amido represents a group of formula: —C(=O)NR'R", wherein R' and R" are independently selected from H, $C_1$ to $C_{10}$ alkyl and aryl. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R' and R", together with the nitrogen atom to which they are attached, form a heterocyclic structure as in, for example, piperidinocarbonyl, morpholinocarbonyl, thiomorpholinocarbonyl, and piperazinocarbonyl.

As used herein the term acylamido represents a group of formula: —NR$^1$C(═O)R$^2$, wherein R$^1$ is an amide substituent, for example, hydrogen, a C$_1$ to C$_{10}$ alkyl group, a C$_3$ to C$_{20}$ heterocyclyl group, an aryl group, preferably hydrogen or a C$_1$ to C$_{10}$ alkyl group, and R$^2$ is an acyl substituent, for example, a C$_1$ to C$_{10}$ alkyl group, a C$_3$ to C$_{20}$ heterocyclyl group, or an aryl group. Preferably R$^1$ is hydrogen and R$^2$ is a C$_1$ to C$_{10}$ alkyl group. Examples of acylamide groups include, but are not limited to, —NHC(═O)CH$_3$, —NHC(═O)CH$_2$CH$_3$, —NHC(═O)Ph, —NHC(═O)C$_{15}$H$_{31}$ and —NHC(═O)C$_9$H$_{19}$. Thus, a substituted C$_1$ to C$_{10}$ alkyl group may comprise an acylamido substituent defined by the formula —NHC(═O)—C$_1$ to C$_{10}$ alkyl, such as —NHC(═O)C$_5$H$_{11}$ or —NHC(═O)C$_9$H$_{19}$. R$^1$ and R$^2$ may together form a cyclic structure, as in, for example, succinimidyl, maleimidyl, and phthalimidyl:

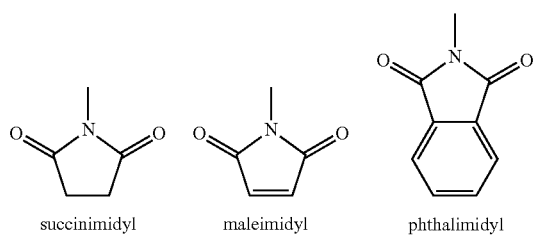

succinimidyl     maleimidyl     phthalimidyl

A C$_1$ to C$_{10}$ alkylthio group is a said C$_1$ to C$_{10}$ alkyl group, preferably a C$_1$ to C$_6$ alkyl group, attached to a thio group. An arylthio group is an aryl group, preferably a phenyl group, attached to a thio group.

A C$_1$ to C$_{10}$ alkoxy group is a said substituted or unsubstituted C$_1$ to C$_{10}$ alkyl group attached to an oxygen atom. A C$_1$ to C$_6$ alkoxy group is a said substituted or unsubstituted C$_1$ to C$_6$ alkyl group attached to an oxygen atom. A C$_1$ to C$_4$ alkoxy group is a substituted or unsubstituted C$_1$ to C$_4$ alkyl group attached to an oxygen atom. Said C$_1$ to C$_{10}$, C$_1$ to C$_6$ and C$_1$ to C$_4$ alkyl groups are optionally interrupted as defined herein. Examples of C$_1$ to C$_4$ alkoxy groups include, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy). Further examples of C$_1$ to C$_{20}$ alkoxy groups are —O(Adamantyl), —O—CH$_2$-Adamantyl and —O—CH$_2$—CH$_2$-Adamantyl. An aryloxy group is a substituted or unsubstituted aryl group, as defined herein, attached to an oxygen atom. An example of an aryloxy group is —OPh (phenoxy).

Unless otherwise specified, included in the above are the well known ionic, salt, solvate, and protected forms of these substituents. For example, a reference to carboxylic acid, carboxy or carboxyl group (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxy or hydroxyl group (—OH) also includes the anionic form (—O$^-$), a salt or solvate thereof, as well as conventional protected forms.

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_1$ to C$_7$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto, enol, and enolate forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

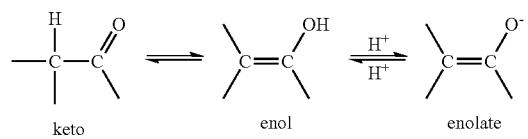

keto     enol     enolate

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting known methods, in a known manner.

Unless otherwise specified, a reference to a particular compound or complex also includes ionic, salt, solvated and protected forms.

Methods of the Invention

The invention provides a method of imaging arthritis in a subject, comprising administering to the subject a tracer which comprises a peptide conjugated to a radionuclide, and imaging the subject by 2D nuclear imaging or by 3D detection of single-photon emission events.

Often, the imaging method used will comprise the use of a gamma camera. A gamma camera is a device which is typically used to image gamma radiation-emitting radioisotopes, also known as radionuclides. Gamma cameras are common equipment in many settings such as hospitals and research laboratories. Many gamma cameras are available, and any suitable camera may be used.

Use of a gamma camera may result in either 2D or 3D images. For example, in the technique known as scintigraphy, 2D images are produced. Scintigraphy is a suitable technique which may be used in the methods of the invention. The terms "2D scintigraphy" and "planar nuclear imaging" may be used interchangeably, and refer to the generation of 2D images by detection of gamma radiation emitted from a radionuclide in a subject.

3D images may be produced by the related technique known as SPECT (single-photon emission computed tomography). SPECT can be considered as a 3D equivalent to planar nuclear imaging. Thus, often, in the methods of the invention, imaging the subject comprises imaging the subject by 2D scintigraphy using a gamma camera or by single photon emission computational tomography (SPECT).

However, SPECT should not be confused with PET (positron emission tomography). In SPECT, the gamma radiation which may be emitted from a radionuclide is directly detected. In contrast, PET tracers emit positrons which annihilate with electrons in the immediate vicinity, releasing two gamma-photons which are released in opposite directions. PET therefore detects this "coincident" gamma radiation, whereas SPECT detects single photon emission events. Importantly SPECT can in some cases be conducted using PET tracers, whereas PET cannot necessarily be conducted using SPECT tracers. Thus, typically, in the method of the invention, imaging the subject does not comprise imaging the subject by PET.

Typically, in the methods of the invention, the radionuclide emits gamma radiation. Any suitable nuclide may be used, such as any nuclide which emits gamma radiation. For example, in the methods of the invention, the radionuclide is often selected from $^{99m}$Tc, $^{123}$I, $^{131}$I, $^{125}$I, $^{67}$Ga, $^{111}$In, $^{133}$Xe, $^{18}$F, $^{68}$Ga, $^{64}$Cu, and $^{201}$Tl. Sometimes, the radionuclide may be selected from $^{99m}$Tc, $^{123}$I, $^{131}$I, $^{125}$I, $^{67}$Ga, $^{111}$In, $^{133}$Xe, $^{18}$F, $^{64}$Cu, and $^{201}$Tl. Thus, in some cases, the radionuclide is not $^{68}$Ga. Sometimes, however, the radionuclide is selected from $^{99m}$Tc, $^{123}$I, $^{131}$I, $^{125}$I, $^{67}$Ga, $^{111}$In, $^{133}$Xe, $^{68}$Ga, $^{64}$Cu, and $^{201}$Tl. Thus, in some cases, the radionuclide is not $^{18}$F. Typically, the radionuclide is selected from $^{99m}$Tc, $^{123}$I, $^{131}$I, $^{125}$I, $^{67}$Ga, $^{111}$In, $^{133}$Xe and $^{201}$Tl. More usually, the radionuclide is selected from $^{99m}$Tc, $^{123}$I, $^{131}$I, $^{125}$I, $^{67}$Ga, $^{111}$In, and $^{201}$Tl. Still more typically, the radionuclide is selected from $^{99m}$Tc, $^{123}$I, $^{131}$I, $^{125}$I, and $^{111}$In. Most typically, in the methods of the invention, the radionuclide is $^{99m}$Tc.

The methods of the invention are useful for imaging arthritis in a subject. Usually, the arthritis is inflammatory arthritis, as defined herein.

In the methods of the invention, the peptide usually comprises a R-G-D moiety, wherein R represents arginine, N-methyl arginine or an arginine mimetic; G represents glycine; and D represents aspartic acid, aspartate or a salt thereof Arginine mimetics include compounds wherein the side-chain of arginine is interrupted by or replaced with one or more moieties such as a heterocyclic moiety e.g. piperidine, an aryl moiety e.g. benzene or a heteroaryl moiety e.g. pyridine or isoquinoline. Exemplary arginine mimetics include compounds such as 2-amino-3-(4-carbamimidoylphenyl)propanoic acid, 2-amino-3-(1-carbamimidoylpiperidin-4-yl)propanoic acid, 2-amino-2-(1-aminoisoquinolin-6-yl)acetic acid, and the like. Other arginine mimetic compounds are well known.

Usually, in a R-G-D moiety, R represents arginine or N-methyl arginine, and most usually R is arginine. Usually, D represents aspartic acid or aspartate and most usually D represents aspartic acid. When multiple R-G-D moieties are present in a peptide, each R-G-D moiety can be the same or different.

Typically, the tracer used in the methods of the invention comprises a peptide which comprises only one R-G-D moiety. Thus, sometimes, the methods of the invention comprise administering to a subject a tracer which comprises a peptide which comprises one R-G-D moiety but does not comprise 2 or more R-G-D moieties. In other cases, a tracer may comprise more than one R-G-D moieties. The number of R-G-D moieties in the peptide present in the tracer is not particularly limited. For example, the methods of the invention may comprise the use of a tracer which comprises from 2 to 10 R-G-D moieties, wherein each R is independently selected from arginine and N-methyl arginine; each G is glycine; and each D is independently selected from aspartic acid, aspartate and a salt thereof. For the avoidance of doubt, a tracer which comprises a peptide which comprises only one R-G-D moiety will usually comprise one or more other atoms or moieties, but will not comprise more than one R-G-D moiety as defined herein.

For example, the tracer used in the methods of the invention may comprise a peptide which comprises from 2 to 5 R-G-D moieties, or may comprise 2 or 3 R-G-D moieties. When the tracer comprises from 2 to 5 R-G-D moieties, it often does not comprise 6 or more R-G-D moieties. When the tracer comprises 2 or 3 R-G-D moieties, it often does not comprise 4 or more R-G-D moieties.

Often, in the methods of the invention, the peptide comprises a cyclised R-G-D moiety according to Formula (I)

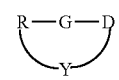

[Formula (I)]

In Formula (I), R represents arginine, N-methyl arginine or an arginine mimetic; G represents glycine; and D represents aspartic acid, aspartate or a salt thereof. Usually, however, in Formula (I), R represents arginine or N-methyl arginine, G represents glycine, and D represents aspartic acid, aspartate or a salt thereof. More usually, in Formula (I), R represents arginine or N-methyl arginine, G represents glycine, and D represents aspartic acid, and typically R represents arginine, G represents glycine, and D represents aspartic acid.

In Formula (I), Y is a linker group. Typically, a moiety of Formula (I) is connected to the remainder of the molecule via one or more bonds from Y. In some cases, a moiety of Formula (I) may be connected to the remainder of the peptide via one or more bonds from R, G and/or D. The remainder of the peptide typically comprises a group capable of coordinating to the radionuclide, such as a chelating group. Thus, Y is typically substituted by or interrupted by the remainder of the peptide, and usually Y is substituted by the remainder of the peptide.

Y can be any suitable linker group. For example, often Y is a linker group is selected from -(Pep)-(Alk)-(Pep)-; -(Pep)-; -(Alk)-; -(Alk)-(Pep)-; -(Pep)-(Alk)-; and -(Alk)-(Pep)-(Alk)-. Typically, Y is a linker group selected from -(Pep)-(Alk)-(Pep)-; -(Alk)-(Pep)-; -(Pep)-(Alk)- and -(Pep)-. More usually, Y is selected from -(Pep)-(Alk)-(Pep)- and -(Pep)-.

Each (Alk) group is independently selected from $C_1$ to $C_{10}$ alkylene or $C_2$ to $C_{10}$ alkenylene. Often, (Alk) is a $C_1$ to $C_{10}$ alkylene group, such as a $C_1$ to $C_6$ alkylene group e.g. a $C_1$ to $C_4$ alkylene group or a $C_1$ to $C_3$ alkylene. Sometimes, (Alk) is a $C_1$ to $C_2$ alkylene group e.g. a methylene group.

Each (Alk) group may independently optionally terminate in and/or be interrupted by one or more groups selected from a $C_6$ to $C_{10}$ arylene group, a $C_5$ to $C_{10}$ heteroarylene group, a $C_3$ to $C_{10}$ cycloalkylene group, a $C_3$ to $C_{10}$ heterocyclylene group, —O—, —S—, —NR$^a$—, —C(O)—, —NR$^a$C(O)—, and —C(O)NR$^a$—. When (Alk) terminates in a group and/or is interrupted by a group as described herein, typically (Alk) terminates in and/or is interrupted by 1, 2 or 3 groups selected from a $C_6$ to $C_{10}$ arylene group, a $C_5$ to $C_{10}$ heteroarylene group, —O—, —S—, —C(O)—, —NR$^a$C(O)—, and —C(O)NR$^a$—. When (Alk) terminates in a group and/or is interrupted by a group as described herein, (Alk) is more typically terminated in and/or interrupted by 1 or 2 groups selected from a $C_6$ to $C_{10}$ arylene group, —O—, —S—, —C(O)—, —NR$^a$C(O)—, and —C(O)NR$^a$—. For example, (Alk) may optionally be interrupted by a $C_6$ to $C_{10}$ arylene group and/or (Alk) may optionally terminate in or be interrupted by 1 or 2 groups selected from —S— and —C(O)—.

Each (Alk) group is independently unsubstituted or is substituted by from 1 to 3 substituents selected from halogen, —OR$^a$, —N(R$^a$)$_2$ and —((CH$_2$)$_n$Het)$_m$R$^b$HetR$^a$. More typically, each (Alk) group is unsubstituted or is substituted by 1 or 2 substituents selected from —OR$^a$, —N(R$^a$)$_2$ and —((CH$_2$)$_n$Het)$_m$R$^b$HetR$^a$. Often, each (Alk) group is unsubstituted or is substituted by 1 or 2 substituents selected from —OR$^a$, —N(R$^a$)$_2$ and —((CH$_2$)$_n$Het)$_m$R$^b$HetR$^a$.

Typically, n is 1 or 2, and often n is 2. When multiple n are present (such as when m>1), each n may be the same or different.

Typically, m is an integer from 1 to 6. Often, m is an integer from 2 to 6, such as from 3 to 6, e.g. from 3 to 5 or 4 to 6. For example, m may be 3, 4, 5 or 6.

Typically, each Het is independently —O— or —NR$^a$—. For the avoidance of doubt, each Het group may be the same or different. Typically, at least one Het is —O—. Sometimes, at least one Het is —O— and at least one Het is —NR$^a$—. Often, Het is —O—.

Typically, R$^b$ is absent or is $C_1$ to $C_6$ alkylene which is optionally substituted by from 1 to 3 oxo groups and/or is interrupted by from 1 to 3 groups selected from —O— and —C(O)—

Typically, each R$^a$ is independently selected from H and $C_1$ to $C_4$ alkyl. More typically, each R$^a$ is selected from H and $C_1$ to $C_2$ alkyl, such as H or methyl. Most typically, each R$^a$ is H. For the avoidance of doubt, when multiple R$^a$ are present, each R$^a$ may be the same or different.

Each (Pep) group is independently an amino acid or a peptide chain, wherein each (Pep) group comprises from 1 to 6 amino acid residues each of which is optionally further derivatized. Often, each (Pep) group comprises from 1 to 4 amino acid residues each of which is optionally further derivatized. Typically, each (Pep) group comprises from 1 to 3 amino acid residues each of which is optionally further derivatized. Thus, often each (Pep) group does not comprise 7 or more amino acid residues; more often each (Pep) group does not comprise 5 or more amino acid residues, and still more often each (Pep) group does not comprise 4 or more amino acid residues. Usually, therefore, each (Pep) group consists of from 1 to 6 amino acid residues each of which is optionally further derivatized; more usually each (Pep) group consists of from 1 to 4 amino acid residues each of which is optionally further derivatized, and most usually each (Pep) group consists of from 1 to 3 amino acid residues each of which is optionally further derivatized.

For example, a method of the invention may comprise administering to the subject a tracer which comprises a peptide of Formula (I) wherein Y is a linker group is selected from -(Pep)-(Alk)-(Pep)-; -(Pep)-; -(Alk)-; -(Alk)-(Pep)-; -(Pep)-(Alk)-; and -(Alk)-(Pep)-(Alk)-; wherein
each (Alk) group is independently selected from $C_1$ to $C_{10}$ alkylene or $C_2$ to $C_{10}$ alkenylene; wherein each (Alk) group may independently optionally terminate in and/or be interrupted by one or more groups selected from a $C_6$ to $C_{10}$ arylene group, a $C_5$ to $C_{10}$ heteroarylene group, a $C_3$ to $C_{10}$ cycloalkylene group, a $C_3$ to $C_{10}$ heterocyclylene group, —O—, —S—, —NR$^a$—, —C(O)—, —NR$^a$C(O)—, and —C(O)NR$^a$—; wherein each (Alk) group is independently unsubstituted or is substituted by from 1 to 3 substituents selected from halogen, —OR$^a$, —N(R$^a$)$_2$ and —((CH$_2$)$_n$Het)$_m$R$^b$-HetR$^a$ wherein n is 1 or 2, m is an integer from 1 to 6 and Het is —O— or —NR$^a$—

R$^b$ is absent or is $C_1$ to $C_6$ alkylene which may optionally be substituted by from 1 to 3 oxo groups and/or be interrupted by from 1 to 3 groups selected from —O— and —C(O)— each R$^a$ is independently selected from H and $C_1$ to $C_4$ alkyl; and each (Pep) group is independently an amino acid or a peptide chain, wherein each (Pep) group comprises from 1 to 6 amino acid residues each of which is optionally further derivatized.

More often, a method of the invention may comprise administering to the subject a tracer which comprises a peptide of Formula (I) wherein Y is a linker group is selected from -(Pep)-(Alk)-(Pep)- and -(Pep)-; wherein:
each (Pep) group is independently an amino acid or a peptide chain, wherein each (Pep) group comprises from 1 to 4 amino acid residues each of which is optionally further derivatized;

(Alk) is a $C_1$ to $C_{10}$ alkylene group; wherein (Alk) may optionally terminate in or be interrupted by 1, 2 or 3 groups selected from a $C_6$ to $C_{10}$ arylene group, a $C_5$ to $C_{10}$ heteroarylene group, —O—, —S—, —C(O)—, —NR$^a$C(O)—, and —C(O)NR$^a$—; wherein (Alk) is unsubstituted or is substituted by 1 or 2 substituents selected from —OR$^a$, —N(R$^a$)$_2$ and —((CH$_2$)$_n$Het)$_m$R$^b$HetR$^a$; wherein n is 1 or 2, m is an integer from 1 to 6 and Het is —O— or —NR$^a$—

R$^b$ is absent or is $C_1$ to $C_6$ alkylene which may optionally be substituted by from 1 to 3 oxo groups and/or be interrupted by from 1 to 3 groups selected from —O— and —C(O)— each R$^a$ is independently selected from H and $C_1$ to $C_4$ alkyl.

More typically, a method of the invention may comprise administering to the subject a tracer which comprises a peptide of Formula (I) wherein Y is a linker group is selected from -(Pep)-(Alk)-(Pep)- and -(Pep)-; wherein:
each (Pep) group is independently an amino acid or a peptide chain, wherein each (Pep) group comprises from 1 to 3 amino acid residues each of which is optionally further derivatized;

(Alk) is a $C_1$ to $C_{10}$ alkylene group; wherein (Alk) may optionally terminate in and/or be interrupted by 1 or 2 groups selected from a $C_6$ to $C_{10}$ arylene group, —O—, —S—, —C(O)—, —NR$^a$C(O)—, and —C(O)NR$^a$—; wherein (Alk) is unsubstituted or is substituted by 1 or 2 substituents selected from —OR$^a$, —N(R$^a$)$_2$ and —((CH$_2$)$_n$Het)$_m$R$^b$HetR$^a$ wherein m is an integer from 1 to 4; n is 1 and Het is —O— or —NR$^a$—

R$^b$ is absent or is $C_1$ to $C_6$ alkylene which may optionally be substituted by from 1 to 3 oxo groups and/or be interrupted by from 1 to 3 groups selected from —O— and —C(O)— each R$^a$ is independently selected from H and $C_1$ to $C_4$ alkyl.

Sometimes, Y is selected from -(Pep1)- and -(Pep2)-(Alk)-(Pep3)-, and more often Y is -(Pep2)-(Alk)-(Pep3)-.

(Pep1) is a peptide chain comprising from 2 to 3 amino acid residues each of which is optionally further derivatized; wherein (Pep1) comprises (i) a first amino acid selected from phenylalanine, tyrosine, tryptophan and histidine, and (ii) a second amino acid selected from lysine, arginine, asparagine and glutamine. When (Pep1) comprises 3 amino acid residues, (Pep1) comprises a third amino acid residue which is not limited. When (Pep1) comprises only 2 amino acid residues, the third amino acid residue is absent. Thus, (Pep1) typically consists of from 2 to 3 amino acid residues each of which is optionally further derivatized. (Pep1) is often a peptide chain consisting of 2 amino acid residues comprising a first amino acid residue selected from tyrosine and tryptophan and a second amino acid residue selected from lysine and asparagine. (Pep1) is more often a peptide chain consisting of 2 amino acid residues comprising a first amino acid residue which is tyrosine and a second amino acid residue which is lysine.

(Pep2) is a peptide chain comprising from 2 to 3 amino acid residues each of which is optionally further derivatized, wherein (Pep2) comprises (i) a first amino acid selected from aspartic acid, glutamic acid, asparagine, glutamine, lysine and arginine, and (ii) a second amino acid selected from cysteine and methionine. When (Pep2) comprises 3 amino acid residues, (Pep2) comprises a third amino acid residue which is not limited. When (Pep2) comprises only 2 amino acid residues, the third amino acid residue is absent. Thus, (Pep2) typically consists of from 2 to 3 amino acid residues each of which is optionally further derivatized. (Pep2) is often a peptide chain consisting of 2 amino acid residues comprising a first amino acid residue selected from aspartic acid, glutamic acid, asparagine, lysine and arginine, and a second amino acid residue which is cysteine. (Pep2) is more often a peptide chain consisting of 2 amino acid residues comprising a first amino acid residue which is selected from aspartic acid, glutamic acid, and lysine and a second amino acid residue which is cysteine. For example, (Pep2) may be a peptide chain consisting of 2 amino acid residues comprising a first amino acid residue which is lysine and a second amino acid residue which is cysteine.

(Pep3) is a peptide chain comprising from 2 to 3 amino acid residues each of which is optionally further derivatized, wherein (Pep3) comprises (i) a first amino acid selected from valine, leucine, isoleucine, methionine, phenylalanine, tyrosine and tryptophan, and (ii) a second amino acid selected from cysteine and methionine. When (Pep3) comprises 3 amino acid residues, (Pep3) comprises a third amino acid residue which is not limited. When (Pep3) comprises only 2 amino acid residues, the third amino acid residue is absent. Thus, (Pep3) typically consists of from 2 to 3 amino acid residues each of which is optionally further derivatized. (Pep3) is often a peptide chain consisting of 3 amino acid residues comprising a first amino acid residue selected from valine, leucine, isoleucine, methionine, phenylalanine, tyrosine and tryptophan, and a second amino acid residue which is cysteine. (Pep3) is more often a peptide chain consisting of 2 amino acid residues comprising a first amino acid residue which is selected from valine, leucine, isoleucine, phenylalanine, and tyrosine and a second amino acid residue which is cysteine. For example, (Pep2) may be a peptide chain consisting of 2 amino acid residues comprising a first amino acid residue which is phenylalanine and a second amino acid residue which is cysteine.

Thus, a method of the invention may comprise administering to the subject a tracer which comprises a peptide of Formula (I) wherein Y is a linker group is selected from -(Pep)-(Alk)-(Pep)- and -(Pep)-; wherein:

(Pep1) is a peptide chain comprising from 2 to 3 amino acid residues each of which is optionally further derivatized; wherein (Pep1) comprises (i) a first amino acid selected from phenylalanine, tyrosine, tryptophan and histidine, e.g. tyrosine, and (ii) a second amino acid selected from lysine, arginine, asparagine and glutamine, e.g. lysine;

(Pep2) is a peptide chain comprising from 2 to 3 amino acid residues each of which is optionally further derivatized, wherein (Pep2) comprises (i) a first amino acid selected from aspartic acid, glutamic acid, asparagine, glutamine, lysine and arginine, e.g. lysine and (ii) a second amino acid selected from cysteine and methionine, e.g. cysteine;

(Pep3) is a peptide chain comprising from 2 to 3 amino acid residues each of which is optionally further derivatized, wherein (Pep3) comprises (i) a first amino acid selected from valine, leucine, isoleucine, methionine, phenylalanine, tyrosine and tryptophan, e.g. phenylalanine and (ii) a second amino acid selected from cysteine and methionine, e.g. cysteine;

(Alk) is a $C_1$ to $C_{10}$ alkylene group; wherein (Alk) may optionally be interrupted by a $C_6$ to $C_{10}$ arylene group and wherein (Alk) may optionally terminate in and/or be interrupted by 1 or 2 groups selected from —S— and —C(O)—.

The method of the invention may comprise administering to a subject a tracer which comprises a peptide which is a compound of Formula (II)

[Formula (II)]

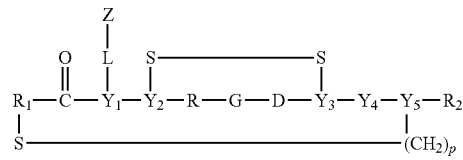

wherein:
R represents arginine or N-methyl arginine;
G represents glycine;
D represents aspartic acid;
$Y_1$ is an amino acid residue selected from aspartic acid, glutamic acid, asparagine, glutamine, lysine and arginine wherein the side-chain of $Y_1$ is bonded via a heteroatom in the side-chain to the moiety -L-Z;
The moieties —$Y_2$—S— and —$Y_3$—S— each independently represent an amino acid residue capable of forming a disulphide bond —$Y_2$—S—S—$Y_3$—;
$Y_4$ is an amino acid residue selected from valine, leucine, isoleucine, methionine, phenylalanine, tyrosine and tryptophan;
The moiety —$Y_5$—$(CH_2)_p$—S— represents a sulphur-containing amino acid residue; wherein p is 1 or 2;
$R_1$ represents —$(CH_2)_q$—$(Ar)_r$—$(CH_2)_s$—, wherein q and s are each independently 0 or an integer, wherein q+s is an integer from 1 to 8, and wherein r is 0 or 1; and wherein Ar is a $C_6$ arylene group;
$R_2$ is absent or represents -Het-$((CH_2)_n$Het$)_m R^b$Het$R^a$;
n is 1 or 2;
m is an integer from 1 to 6;
each Het is independently —O— or —$NR^a$—;

$R^b$ is absent or is $C_1$ to $C_6$ alkylene which may be optionally substituted by from 1 to 3 oxo groups and/or may be interrupted by from 1 to 3 groups selected from —O— and —C(O)—;

each $R^a$ is independently selected from H and $C_1$ to $C_2$ alkyl;

L is —C(O)—($C_1$-$C_6$ alkylene)-C(O)—; wherein the alkylene group of L may be optionally interrupted by —O— and/or wherein the alkylene group of L is unsubstituted or substituted by 1 or 2 substituents selected from —OH, $C_1$ to $C_2$ alkoxy and $C_1$ to $C_2$ alkyl;

Z represents a moiety capable of coordinating to the radionuclide.

In Formula (II), R typically represents arginine. $Y_1$ is typically an amino acid residue selected from aspartic acid, glutamic acid, and lysine wherein the side-chain of $Y_1$ is bonded via a heteroatom in the side-chain to the moiety -L-Z; and more typically $Y_1$ is lysine. Either or both of the moieties —$Y_2$—S— and —$Y_3$—S— typically independently represent cysteine, and more typically each of the moieties —$Y_2$—S— and —$Y_3$—S— represents cysteine. $Y_4$ is often an amino acid residue selected from valine, leucine, isoleucine, phenylalanine, and tyrosine; more often $Y_4$ is selected from phenylalanine and tyrosine, and most often $Y_4$ is phenylalanine. The moiety —$Y_5$—$(CH_2)_p$—S— typically represents methionine or cysteine or a derivative thereof, and more typically —$Y_5$—$(CH_2)_p$—S— represents cysteine; thus typically p is 1.

In Formula (II), q+s is typically an integer from 1 to 6, such as from 1 to 4 or from 1 to 3, e.g. 1 or 2. $R_2$ typically represents -Het-$((CH_2)_n Het)_m R^b Het R^a$; thus $R_2$ is typically present. n is often 1, and m is often an integer from 3 to 6, e.g. from 2 to 5, such as from 3 to 4. Often, it is the case that not all Het groups present in Formula (II) will be the same. Most often, at least one Het group is —O—. Sometimes, more than one Het group is —O—. Most usually, Het is —O—. Often, each $R^a$ is independently selected from H and $C_1$ to $C_2$ alkyl, such as H or methyl, e.g. H.

In Formula (II), $R^b$ is absent or is $C_1$ to $C_6$ alkylene which may be optionally substituted by from 1 to 3 oxo groups and/or may be interrupted by from 1 to 3 groups selected from —O— and —C(O)—. If $R^b$ is substituted by an oxo group then this means that two of the hydrogen atoms on an individual carbon atom of $R^b$ are replaced by one oxygen atom which is double-bonded to the carbon atom to form a carbonyl group. $R^b$ is often substituted by 1 or 2 oxo groups, and thus $R^b$ is often a di-carbonyl moiety. $R^b$ is often interrupted by 1 or 2 groups selected from —O— and —C(O)—, more often by 1 group selected from —O— and —C(O)—. When $R^b$ is interrupted, $R^b$ is usually interrupted by —O—, thus $R^b$ is most often interrupted by one —O— group.

In Formula (II), $R^b$ is often a $C_3$ to $C_6$ alkylene group such as a $C_3$, $C_4$ or $C_5$ alkylene group. For example, $R^b$ may be a $C_4$ alkylene group which is substituted by 1 or 2 oxo groups and is interrupted by 1 or 2 groups selected from —O— and —C(O)—, e.g. by 1 —O— group. For example, $R^b$ is sometimes —C(O)—$(CH_2)_d$—O—$(CH_2)_d$—C(O)— wherein each d is independently 1, 2 or 3; thus for example $R^b$ may be —C(O)—$(CH_2)_2$—O—$(CH_2)_2$—C(O)—.

In Formula (II), L is —C(O)—($C_1$-$C_6$ alkylene)-C(O)—; wherein the alkylene group of L may be optionally interrupted by —O— and/or wherein the alkylene group of L is unsubstituted or substituted by 1 or 2 substituents selected from —OH, $C_1$ to $C_2$ alkoxy and $C_1$ to $C_2$ alkyl. Often, the alkylene group of L is a $C_2$ to $C_4$ alkylene group such a $C_3$ or a $C_4$ alkylene group. Usually, L is unsubstituted or is substituted by 1 substituent selected from —OH, $C_1$ to $C_2$ alkoxy and $C_1$ to $C_2$ alkyl; more often L is unsubstituted or is substituted by 1 substituent selected from —OH, methoxy and methyl. Most often L is unsubstituted.

In Formula (II), Z represents a moiety capable of coordinating to the radionuclide. Z often represents a moiety which chelates the radionuclide. For example, Z may be a moiety of Formula (III)

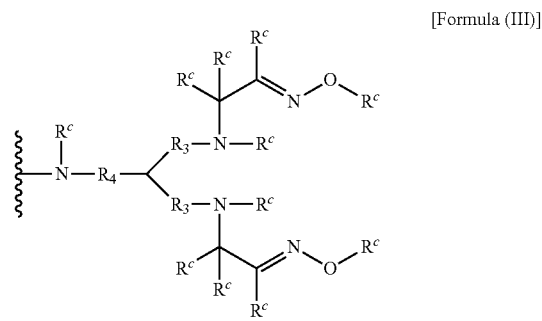

[Formula (III)]

wherein:
each group $R^c$ is independently H or $C_1$ to $C_2$ alkyl;
each group $R_3$ is independently $C_1$ to $C_3$ alkylene;
$R_4$ is $C_1$ to $C_4$ alkylene; and
each alkyl group and/or each alkylene group is unsubstituted or is substituted with 1 substituent selected from —OH, —N($R^a)_2$, $C_1$ to $C_2$ alkyl, and $C_1$ to $C_2$ alkoxy.

In Formula (III), each $R^c$ is often independently H or methyl; more often each $R^c$ is independently H. For the avoidance of doubt, each $R^c$ group may be the same or different. In Formula (III), each $R_3$ group is often independently $C_2$ or $C_3$ alkylene such as $C_2$ alkylene. For the avoidance of doubt, each $R_3$ group may be the same or different. $R_4$ is typically $C_1$ to $C_3$ alkylene such as $C_2$ or $C_3$ alkylene e.g. $C_2$ alkyene. Each $R_3$ group and $R_4$ group is often independently unsubstituted, and most often each $R_3$ group and $R_4$ group is unsubstituted. Each $R_3$ and $R_4$ may be the same or different. For example, Z may be a moiety of Formula (IV).

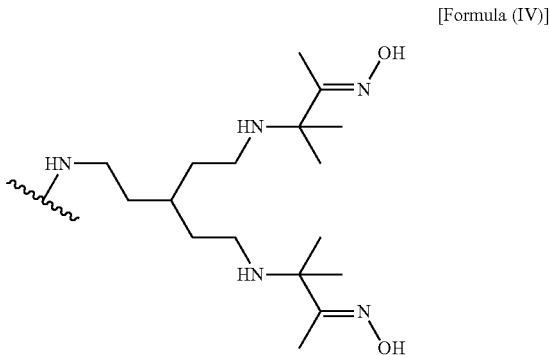 [SMILES: *NCCC(CCNC(C)(C)/C(C)=N/O)CCNC(C)(C)/C(C)=N/O]

[Formula (IV)]

Therefore, the method of the invention may comprise administering to the subject a tracer comprising a peptide wherein the peptide is of Formula (II), wherein
R represents arginine or N-methyl arginine;
G represents glycine;
D represents aspartic acid;

$Y_1$ is an amino acid residue selected from aspartic acid, glutamic acid, and lysine; typically wherein $Y_1$ is lysine; and wherein the side-chain of $Y_1$ is bonded via a heteroatom in the side-chain to the moiety -L-Z;

Either or both of the moieties —$Y_2$—S— and —$Y_3$—S— independently represents cysteine; e.g. both —$Y_2$—S— and —$Y_3$—S— each represent cysteine;

$Y_4$ is an amino acid residue selected from valine, leucine, isoleucine, phenylalanine, and tyrosine; such as an amino acid selected from phenylalanine and tyrosine, e.g. phenylalanine;

The moiety —$Y_5$—$(CH_2)_p$—S— represents cysteine, (i.e. p is 1);

$R_1$ represents —$(CH_2)_q$—$(Ar)_r$—$(CH_2)_s$—, wherein q and s are each independently 0 or an integer, wherein q+s is an integer from 1 to 8, and wherein r is 0 or 1; and wherein Ar is a $C_6$ arylene group;

$R_2$ represents -Het-$((CH_2)_n Het)_m R^b HetR^a$ wherein n is 1 or 2; e.g. $R_2$ is —NH—$((CH_2)_2 Het)_m R^b HetR^a$;

m is an integer from 3 to 6; e.g. 4 or 5.

each Het is independently —O— or —$NR^a$—;

$R^b$ is —C(O)—$(CH_2)_d$—O—$(CH_2)_d$—C(O)— wherein each d is independently 1, 2 or 3; e.g. $R^b$ is —C(O)—$CH_2$—O—$CH_2$—C(O)—;

each $R^a$ is independently selected from H and $C_1$ to $C_2$ alkyl; for example each $R^a$ may be selected from H and methyl, e.g. H.

L is —C(O)—$(C_1$-$C_6$ alkylene)-C(O)—; wherein the alkylene group of L is unsubstituted; e.g. L may be unsubstituted —C(O)—$(C_2$-$C_4$ alkylene)-C(O)—, e.g. —C(O)—$(C_3$ alkylene)-C(O)—;

Z is a moiety of Formula (III), for example a moiety of Formula (IV).

Often, the method of the invention may comprise administering to the subject a tracer comprising a peptide wherein the peptide is of Formula (II), wherein:

R represents arginine;

G represents glycine;

D represents aspartic acid;

$Y_1$ is lysine bonded via the side-chain N to the moiety -L-Z;

—$Y_2$—S— and —$Y_3$—S— each represent cysteine;

$Y_4$ is phenylalanine;

The moiety —$Y_5$—$(CH_2)_p$—S— represents cysteine (i.e. p is 1);

$R_1$ represents —$(CH_2)_q$—$(Ar)_r$—$(CH_2)_s$—, wherein q and s are each independently 0 or 1, wherein q+s is 1 or 2, and wherein r is 0 or 1, and wherein Ar is a $C_6$ arylene group;

$R_2$ represents —NH—$((CH_2)_2 Het)_m$-C(O)—$CH_2$—O—$CH_2$—C(O)-HetR$^a$, wherein m is an integer 4 or 5 and wherein each Het is independently —O— or —$NR^a$—; e.g. often $R_2$ is —NH—$(C_2H_5O)_3$—$C_2H_5NH$—C(O)—$CH_2$—O—$CH_2$—C(O)—$NH_2$ each $R^a$ is H;

L is unsubstituted —C(O)—$(C_2$-$C_4$ alkylene)-C(O)—;

Z is a moiety of Formula (IV).

Typically, the method of the invention may comprise administering to the subject a tracer comprising a peptide wherein the peptide is maraciclatide. Maraciclatide is also known as NC100692, and is produced by GE Healthcare. NC100692 is described in for example US 2013/0129623 A1. NC100692 (GE Healthcare) is a small cyclic peptide containing the RGD tripeptide motif.[23-26] In vitro studies have demonstrated high binding affinity for the $α_vβ_3$ integrin. NC100692 has not been widely prescribed, and prior to the studies described herein a total 81 patients had been given $^{99m}$Tc-NC100962.[23,27] However, in safety assessments no clinically important safety signals or trends were noted. Pharmacokinetic studies in healthy volunteers determined a mean elimination half-life of approximately one hour. A study of immunogenicity in 10 subjects found no detectable antibodies to NC100962 at 4 months.[23]

Maraciclatide has the formula shown in Formula (VI).

[Formula (VI)]

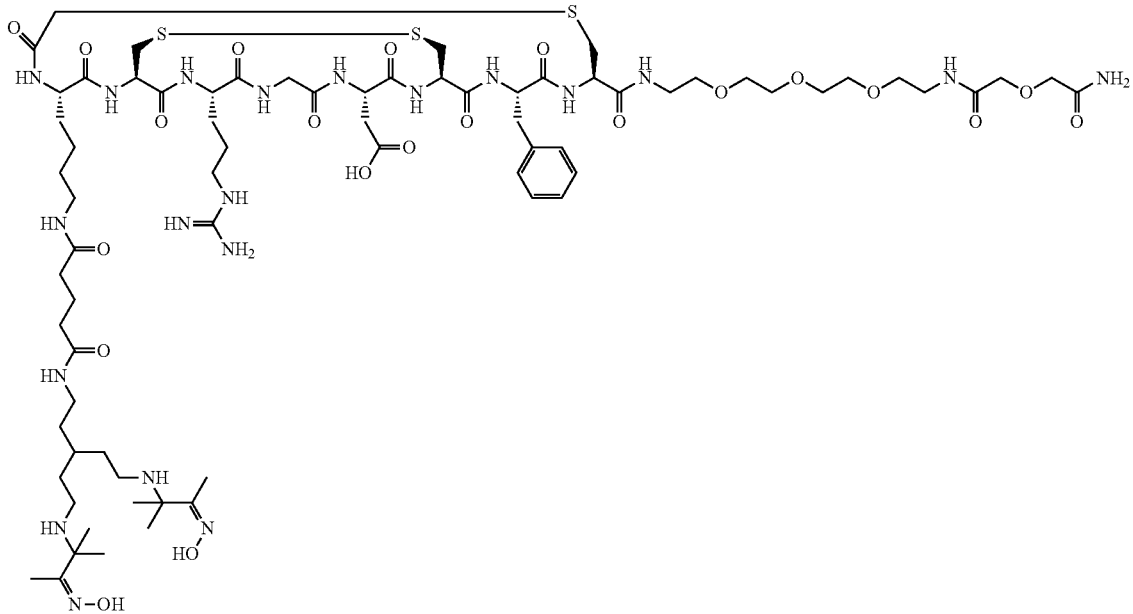

In the tracers used in the methods of the invention, the radionuclide can coordinate to the peptide at any suitable point. Indeed, the radionuclide can be an atom of the peptide. When the method of the invention comprises administration of a tracer which comprises a peptide conjugated to a radionuclide, wherein the radionuclide is an atom of the peptide, the peptide may, but typically does not, also comprise a separate group capable of coordinating to the radionuclide.

In Formula VI, the group of Formula IV is said moiety capable of coordinating to the radionuclide. Accordingly, when the radionuclide is a nuclide which emits gamma radiation, such as $^{99m}$Tc, the radionuclide is typically coordinated to the peptide by coordinating to the moiety of Formula IV.

When the radionuclide is an element as described herein, for example $^{99m}$Tc, the radionuclide often coordinates to the peptide which is maraciclatide as shown in Formula (VIa). Thus the methods of the invention may comprise the use of a tracer wherein the peptide is maraciclatide and the radionuclide is $^{99m}$Tc.

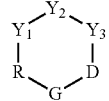

[Formula (V)]

wherein either $Y_1$ or $Y_2$ is tyrosine; and either $Y_2$ or $Y_3$ is lysine, wherein the lysine is bonded at the N(6)-position to the remainder of the peptide. In Formula (V), typically when $Y_1$ is tyrosine and $Y_2$ is lysine, $Y_3$ is absent or is an amino acid residue; when $Y_2$ is tyrosine and $Y_3$ is lysine, $Y_1$ is absent or is an amino acid residue; and/or when $Y_1$ is tyrosine and $Y_3$ is lysine, $Y_2$ is absent or is an amino acid residue. Often $Y_1$ is tyrosine, $Y_3$ is lysine and $Y_2$ is absent.

For the avoidance of doubt, the moiety of Formula (V) is bonded to the remainder of the peptide by one or more bonds. Typically, the one or more bonds to the remainder of the peptide derive from one of the amino acid residues $Y_1$, $Y_2$ and/or $Y_3$. Often, the moiety of Formula (V) is bonded to the reminder of the peptide by a bond from an amino acid which is lysine, for example by the formation of an amide bond from the N(6) atom of the side-chain of lysine.

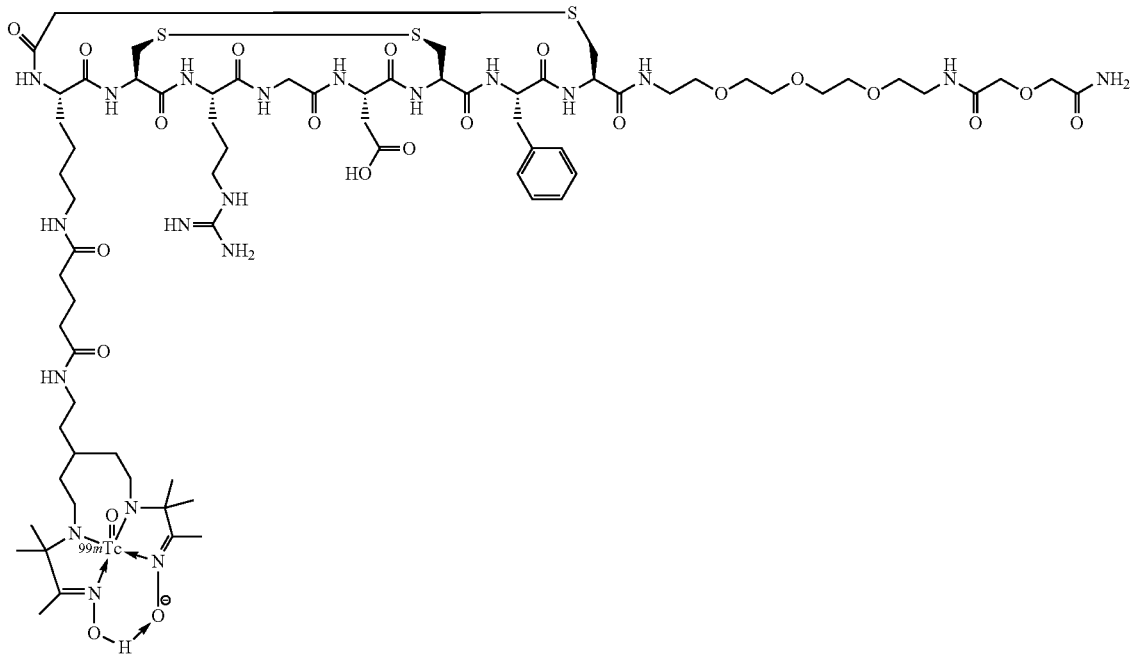

[Formula (VIa)]

As explained herein, the methods of the invention may comprise administration of a tracer which comprises a peptide comprising one or more R-G-D moieties as described herein. Therefore, in the methods of the invention, the peptide often comprises from 2 to 10 R-G-D moieties, wherein each R is independently selected from arginine and N-methyl arginine; each G is glycine; and each D is independently selected from aspartic acid, aspartate and a salt thereof. More usually, the peptide comprises from 2 to 5 R-G-D moieties. Often, the peptide comprises 2 or 3 R-G-D moieties. Sometimes at least one of the R-G-D moieties is present in a moiety of formula (V). Often each of the R-G-D moieties in the peptide is present in moiety of Formula (V)

In the methods of the invention, the tracer may be encapsulated in or conjugated to a drug delivery vehicle. Typically, the drug delivery vehicle is selected from a liposome, a PEGylated liposome, a niosome, an aquasome, a dendrimer, a micelle, an inorganic or organic nanoparticle, a lipid, a poly-amino acid, an emulsion or a hydrogel. More typically, the drug delivery vehicle is selected from a liposome, a PEGylated liposome, a dendrimer, an inorganic or organic nanoparticle and a poly-amino acid. Often, the drug delivery vehicle is selected from a liposome, a PEGylated liposome, a dendrimer, a poly-amino acid. Usually, the drug delivery vehicle is selected from a liposome and a dendrimer.

The methods of the invention are medically useful. The methods of the invention are particularly useful for imaging arthritis in a subject. The methods of the invention as described herein are not only concerned with imaging arthritis with a view to diagnosing the condition. It is just as important to image arthritis to assess disease activity in previously diagnosed inflammatory arthritis (for example, to obtain information about disease progression in patients in whom arthritis has already been diagnosed); to monitor efficacy of treatment regimens; to determine the efficacy of pharmaceuticals and the like. Many uses for and applications of the methods of the invention will occur to the skilled person.

Usually, the arthritis is inflammatory arthritis. For example, the arthritis can be selected from rheumatoid arthritis, ankylosing spondylitis, psoriatic arthritis, entereopathic arthritis, reactive arthritis, gout, pseudo-gout, septic arthritis, osteoarthritis, juvenile idiopathic arthritis, arthritis associated with systemic lupus erythematosus, arthritis associated with one or more spondyloarthropathies, arthritis associated with enthesopathy or enthesitis, arthritis associated with sacroiliitis, arthritis associated with tenosynovitis, tendon inflammation or tendon sheath inflammation, and/or arthritis associated with connective tissue diseases. The arthritis is typically selected from rheumatoid arthritis, ankylosing spondylitis, psoriatic arthritis, entereopathic arthritis, reactive arthritis, gout, pseudo-gout, septic arthritis, osteoarthritis, juvenile idiopathic arthritis, and arthritis associated with systemic lupus erythematosus. Often, the arthritis is selected from rheumatoid arthritis, ankylosing spondylitis, psoriatic arthritis, entereopathic arthritis, and reactive arthritis. Usually, the arthritis is selected from rheumatoid arthritis, ankylosing spondylitis, and psoriatic arthritis, and most often the arthritis is rheumatoid arthritis.

The methods of the invention may comprise imaging the whole body of the subject. Alternatively, the methods of the invention may comprise imaging one or more of the fingers, hands, elbows, shoulders, toes, feet, ankles, knees or hips of the subject, but not comprising imaging the whole body of the subject. Typically, imaging the subject may comprise imaging only the hands and/or the feet of the subject, and in this case imaging typically does not comprise imaging the remainder of the body of the subject. Usually, the methods of the invention comprise imaging an inflamed joint of the subject.

The methods of the invention are useful in imaging arthritis in a subject. The subject is a mammal, in particular a human. However, it may be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters. The subject can be any animal that is capable of suffering from arthritis.

The methods of the invention can be used to image arthritis in a subject in circumstances wherein the subject can be asymptomatic. The subject is typically one that is suffering from arthritis, or is one that is at risk of suffering from arthritis, or is one that has previously experienced arthritis. Alternatively, the methods of the invention can be used to image arthritis in a subject in circumstances wherein the subject can be symptomatic. The subject is typically one that is suffering from arthritis, or is one that is at risk of suffering from arthritis, or is one that has previously experienced arthritis. Typically, the subject is suffering from arthritis. The methods of the invention can be used to detect arthritis in an individual in circumstances where other techniques such as clinical examination may not reveal arthritis. Thus, typically, in the methods of the invention, the subject (i) has suffered from or is suffering from arthritis, or (ii) is susceptible to arthritis.

The methods of the invention may comprise administering to the subject a composition which comprises the tracer and one or more pharmaceutically acceptable excipients and/or diluents and/or carriers.

The methods of the invention may comprise administering to the subject the tracer or a composition which comprises the tracer in a variety of dosage forms. Thus, the tracer or composition can be administered orally, for example as tablets, troches, lozenges, aqueous or oily suspensions, dispersible powders or granules. The tracer may also be administered parenterally, whether subcutaneously, intravenously, intramuscularly, intrasternally, transdermally or by infusion techniques. The tracer may also be administered as a suppository. Most often the tracer is administered orally or parenterally, and most often the tracer is administered parenterally.

In the methods of the invention, the tracer is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or, usually, they may be in the form of sterile, aqueous, isotonic saline solutions. Pharmaceutical compositions suitable for delivery by needleless injection, for example, transdermally, may also be used.

In the methods of the invention, the dose of the tracer (or composition thereof) which is administered to the subject may be determined according to various parameters, especially according to the compound used; the age, weight and condition of the subject to be treated; the route of administration; and the required regimen. A physician will be able to determine the required route of administration and dosage for any particular subject. A typical daily dose of the tracer is from about 0.01 to 100 µg per kg, usually from about 0.1 µg/kg to 50 µg/kg, such as from about 0.1 µg/kg to 10 µg/kg of body weight, e.g. from about 0.5 µg/kg to about 2 µg/kg, according to the activity of the specific tracer or composition thereof, the age, weight and conditions of the subject to be treated, the type and severity of the disease or condition and the frequency and route of administration. Typically, daily dosage levels of the tracer are from 1 µg to 5 mg, more typically from 10 µg to 800 µg, still more typically from about 30 µg to 150 µg, such as about 75 µg. A suitable dose of a composition comprising the tracer can easily be determined by a skilled person based on, for example, the weight percentage of the tracer in the composition.

The methods of the invention may comprise administering to the subject the tracer or a composition which comprises the tracer and one or more pharmaceutically acceptable excipients and/or diluents and/or carriers, wherein the tracer or composition is provided in the form of a kit, which may further comprise instructions to enable the kit to be used in the methods described herein or details regarding which subjects the method may be used for.

The invention also provides the use of a tracer which comprises a peptide conjugated to a radionuclide as an imaging agent for imaging arthritis by 2D nuclear imaging or by 3D detection of single-photon emission events. Typically, the tracer is as defined herein, and/or the imaging method is as defined herein; and/or the arthritis is as defined herein; and/or the subject is as defined herein. More typically, the tracer, the imaging method, the arthritis and the subject are all as defined herein.

The invention also provides a method of diagnosing arthritis in a subject, which method comprises (a) administering to the subject a tracer which comprises a peptide conjugated to a radionuclide; (b) imaging the subject by 2D nuclear imaging or by 3D detection of single-photon emission events; and (c) determining whether or not the subject has arthritis. Typically, the tracer is as defined herein, and/or the imaging method is as defined herein; and/or the arthritis is as defined herein; and/or the subject is as defined herein. More typically, the tracer, the imaging method, the arthritis and the subject are all as defined herein. Determining whether or not the subject has arthritis can be conducted as described herein.

The invention also provides a tracer for use in the diagnosis of arthritis in a subject, wherein the tracer comprises a peptide conjugated to a radionuclide; and wherein the diagnosis comprises (a) administering the tracer to the subject; (b) imaging the subject by 2D nuclear imaging or by 3D detection of single-photon emission events; and (c) determining whether or not the subject has arthritis. Typically, the tracer is as defined herein, and/or the imaging method is as defined herein; and/or the arthritis is as defined herein; and/or the subject is as defined herein. More typically, the tracer, the imaging method, the arthritis and the subject are all as defined herein. Determining whether or not the subject has arthritis can be conducted as described herein.

Determining whether or not the subject has arthritis can be conducted according to any suitable technique. For example, the skilled person may associate accumulation of the tracer as a marker for arthritis. Determining accumulation of the tracer may be conducted relative to a standard such as an image obtained from a different subject or from a panel of different subjects, or from the same subject at a different time, or from a different part of the body of the same subject.

The invention also provides a method of evaluating the activity of a pharmaceutical for the treatment of arthritis, comprising administering a tracer to a subject, wherein the tracer comprises a peptide conjugated to a radionuclide, and wherein the subject has arthritis;
detecting the tracer by imaging the subject by 2D nuclear imaging or by 3D detection of single-photon emission events;
administering the pharmaceutical to the subject;
detecting the tracer by imaging the subject by 2D nuclear imaging or by 3D detection of single-photon emission events after administering the pharmaceutical to the subject; and
evaluating changes in the image of the subject or the detected amount of the tracer before and after administration of the pharmaceutical.

Typically, a decreased response arising from the tracer in the image of the subject obtained after administration of the pharmaceutical compared to that obtained before administration of the pharmaceutical is indicative of efficacy of the pharmaceutical. In a similar manner, a decreased detected amount of the tracer after administration of the pharmaceutical compared to that obtained before administration of the pharmaceutical is indicative of efficacy of the pharmaceutical. Typically, the tracer is as defined herein, and/or the imaging method is as defined herein; and/or the arthritis is as defined herein; and/or the subject is as defined herein. More typically, the tracer, the imaging method, the arthritis and the subject are all as defined herein.

Synthesis

The methods of the invention comprise administration of a tracer. The tracer as described herein can be produced by any suitable method known in the art. Many such methods will occur to the skilled person. For example, a peptide may be synthesized and then conjugated to a group which can coordinate a radionuclide. The composite thus produced may then be coordinated to the radionuclide. Alternatively, a group which is capable of coordinating a radionuclide as described herein can be so coordinated to form a complex or composite, before being conjugated to a peptide as described herein. Any method which is suitable for resulting in the tracers used in the methods of the invention may be used. Any suitable synthetic route may be used to obtain the peptides, radionuclide-coordinating moieties and radionuclides used in the methods of the invention, and many suitable reaction conditions may occur to the skilled person.

For example, peptides as described herein can be produced using any suitable technique. For example, peptides can be synthesized using solid-phase peptide synthesis or by liquid-phase peptide synthesis. Typically solid-phase peptide synthesis is used. Alternatively, peptides can be produced using microbiological techniques by the action of microorganisms. Typical microorganisms include bacteria such as *Escherichia coli* and yeast such as *Saccharomyces cerevisiae*. Suitable microbiological techniques are well known to the skilled person.

Groups capable of coordinating radionuclides as described herein are well known in the art, and can be obtained commercially or synthesized using standard organic chemistry techniques. The radionuclides which are present in the tracers used in the methods of the invention can be commercially obtained.

A skilled organic chemist can easily attach a radionuclide-coordinating group to a ring peptide using known chemistry (e.g. by reacting an amine group on an amino acid with a carboxylic acid group on the coordinating moiety to form an amide bond). Many coupling reactions are known to the skilled person, and many pairs of complementary functional groups that can react together in a coupling reaction are known. Any suitable pair of complementary functional groups can be used. Examples of pairs of complementary functional groups that can react together in a coupling reaction include the reaction of an —NHR group with a C(=X)OR group (for instance the reaction of an —NH$_2$ group with a —C(NH)OMe group, or the reaction between an —NH$_2$ group and a —COOH group), the reaction of an azide group with an alkyne group, and the [4+2] cycloaddition of a diene with a dienophile.

Maraciclatide and similar compounds of Formula (II) can be prepared as described in WO 03/006491.

The following Examples illustrate the invention. They do not however, limit the invention in any way. In this regard, it is important to understand that the particular experiments described in the Examples section are designed only to provide an indication of suitability of the methods of the invention for imaging arthritis.

Examples

Methods

We conducted a pilot proof-of-concept study to investigate $^{99m}$Tc-NC100692 imaging in patients with RA. 5 RA patients with active disease (DAS28 ESR>3.2) were recruited. Patients underwent a full clinical examination including 68/66 tender/swollen joint count and blood was taken for ESR if this was not recently available. An ultrasound scan, using a GE Loqiq 9 ultrasound scanner with a 14 MHz probe with standardised settings, was carried out of 38 joints (bilateral metacarpophalangeal joints, proximal interphalangeal joints, wrists, elbows, shoulders, knees ankles and 2$^{nd}$-5$^{th}$ metatarsophalangeal joints). Images were scored on a semi-quantitative scale from 0-3 for grey-scale (GS) synovial thickening and power Doppler (PD) signal and the scores summed to give total GS and PD scores for each patient.

Within 24 hours of the ultrasound scan and clinical examination patients were injected intravenously with 75 µg of $^{99m}$Tc-NC100692 containing an activity as close as possible to 740 MBq. Images were obtained with a gamma camera at multiple time points over 3 hours. Dynamic images were taken of the hands at 5 minute intervals for the first 45 minutes. Between 60 and 90 minutes static images of the hands, the feet and the whole body were taken. At 120-180 minutes static images of the hands, the feet and the whole body were taken. In addition, a single SPECT/CT image of the hands was acquired. SPECT/CT (single photon emission tomography (SPECT)/computed tomography (CT)) is an imaging technique for acquiring a 3-dimensional image of radioisotope uptake which is overlayed onto a CT image for anatomical localisation.

Planar and SPECT/CT images were scored by an observer blinded to the findings of the clinical examination and the ultrasound. Two methods of scoring were used. Firstly, for planar imaging, each joint (proximal interphalangeal joints, metacarpophalangeal joints, wrists, elbows, sternoclavicular joint, acromioclavicular joint, shoulders, hips, knees, ankles, midtarsal joints and metatarsophalangeal joints) was scored for the presence or absence of uptake and a total derived for each patient (binary scoring). Secondly, for both planar and SPECT/CT imaging, dedicated software was used and a fully quantitative score derived for each joint by drawing a region of interest around the joint and correcting uptake for background. For both scoring methods the individual scores for each joint were summed to give a total score for each patient. Correlation between and clinical and imaging variables was tested with Pearson's correlation coefficient (SPSS 22, IBM).

Results

Figure 2:
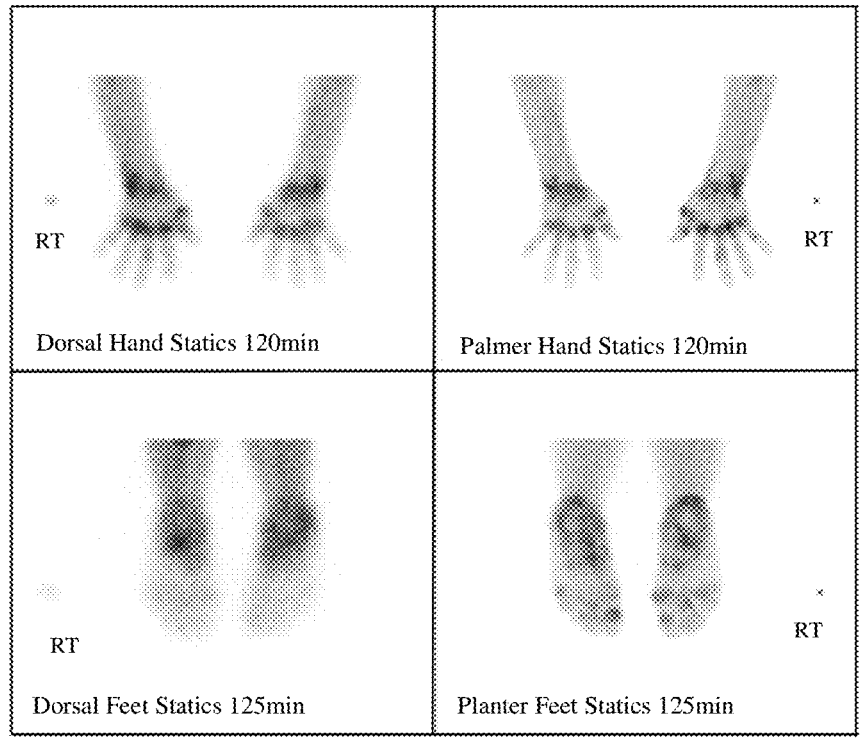
FIG. 2 shows representative static images of the hands and feet from 2 patients taken at 2 hours. Uptake is clearly visible in the wrists, metacarpophalangeal joints, proximal interphalangeal joints, ankles, midfoot and metatarsophalangeal joints.
Figure 2:
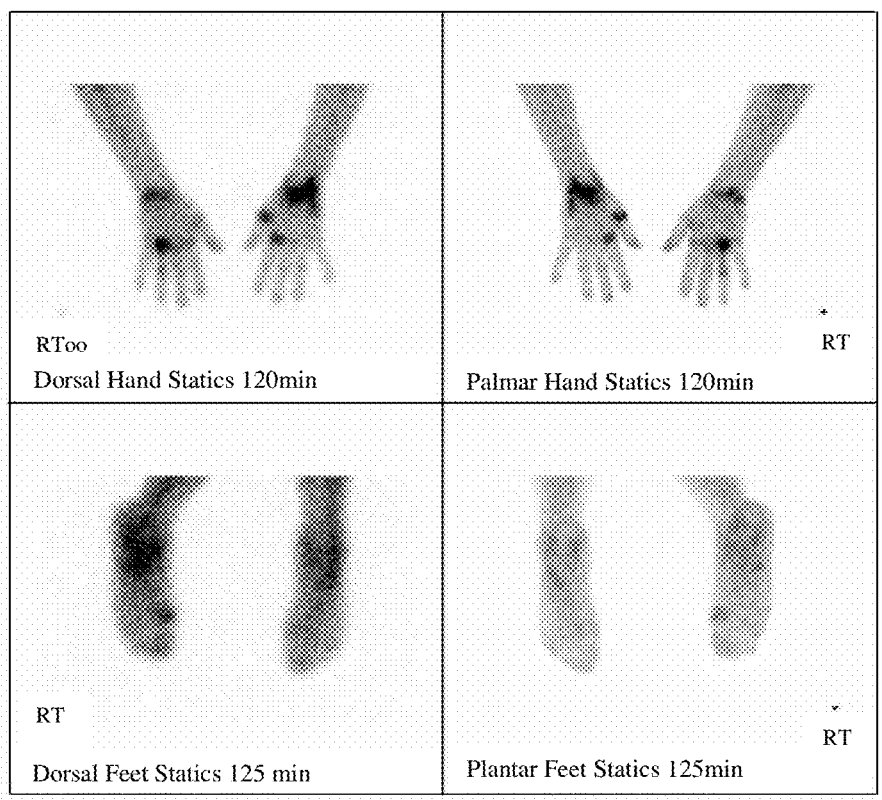
Figure 3:
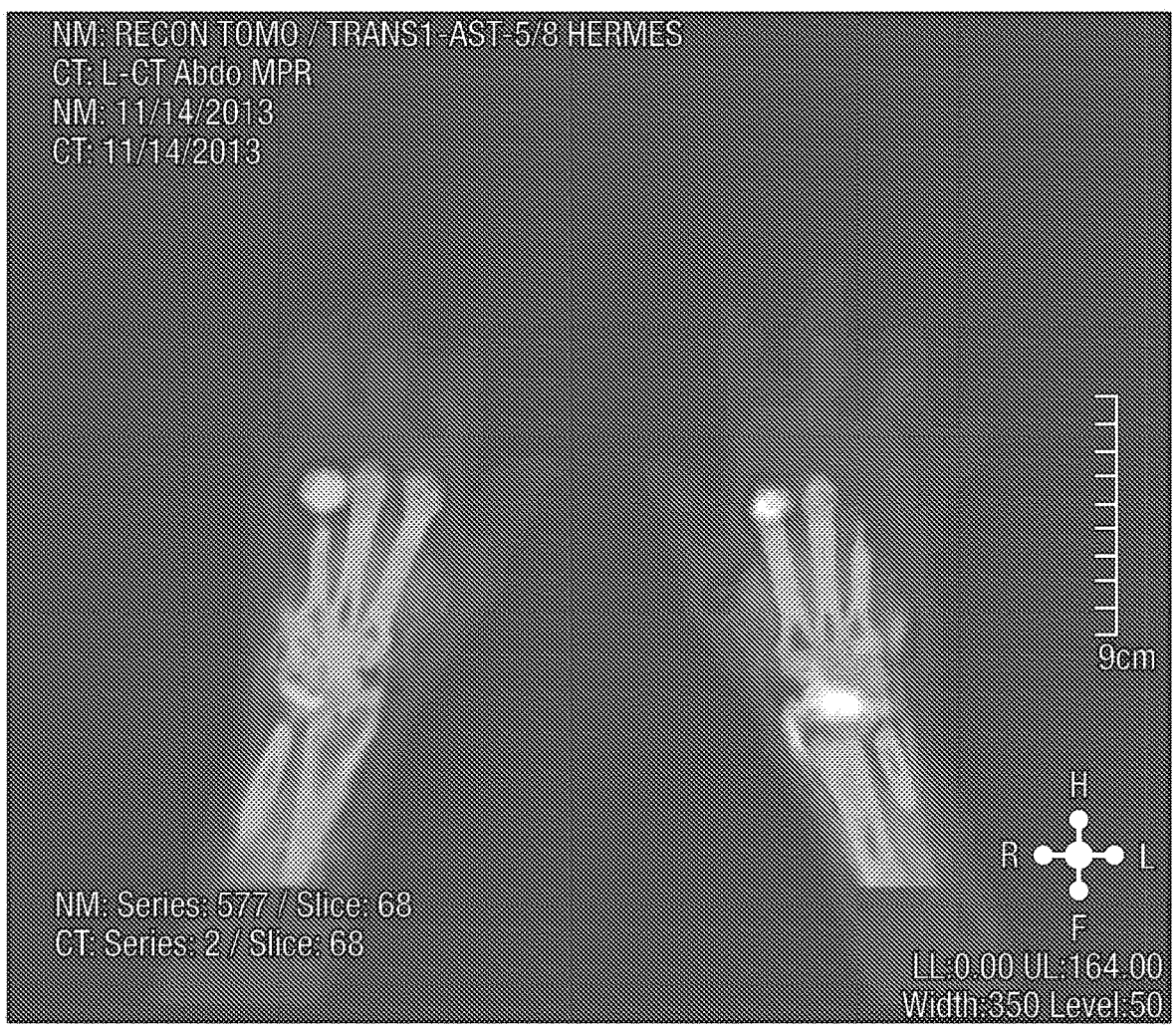
FIG. 3 shows representative SPECT/CT image of the hands. Uptake is seen in the wrists and metacarpophalangeal joints.
Figure 4A:
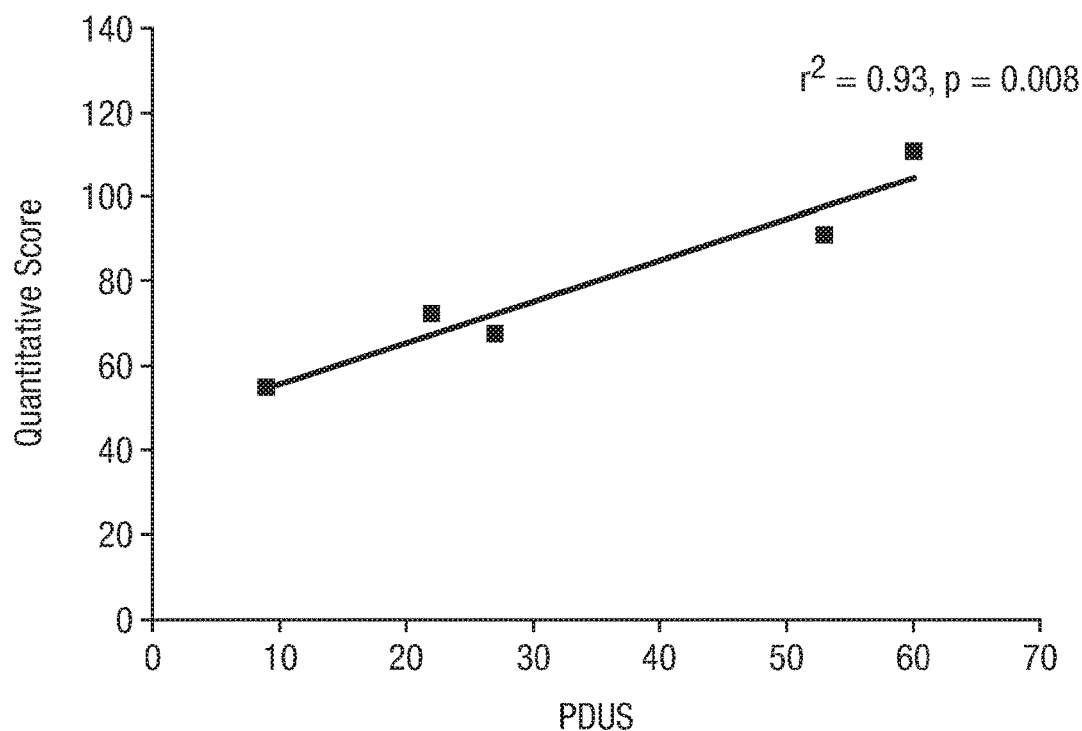
FIG. 4 shows correlation between PDUS and $^{99m}$Tc-NC100692 imaging with quantitative scoring (A) and binary scoring (B).
Figure 4B:
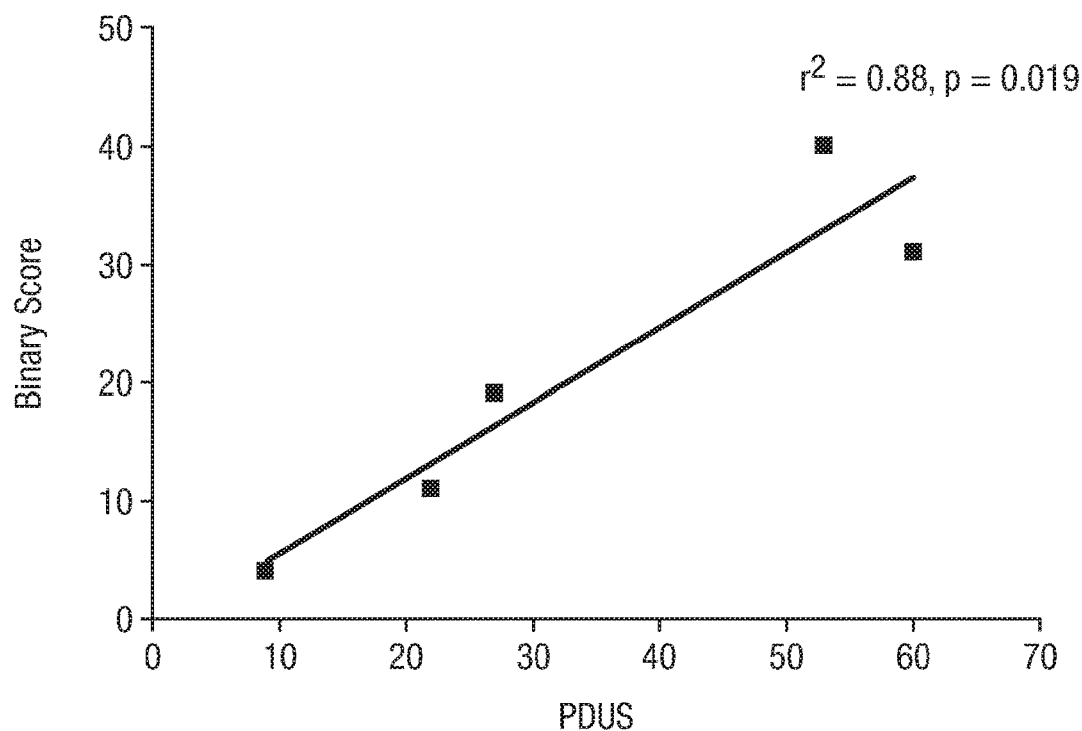

Uptake was clearly seen in the joints of all patients on whole body views and images of the hands and feet as well as SPECT/CT (FIGS. 1-3). Significant correlation was not seen between any imaging and clinical parameters. Strong correlation was seen between PDUS and whole-body quantitative $^{99m}$Tc-NC100692 scores ($r^2$=0.93, p=0.008) (FIG. 4). Strong correlation was also seen between PDUS and binary scores $^{99m}$Tc-NC100692 ($r^2$=0.88, p=0.019). GSUS also correlated strongly with quantitative whole-body $^{99m}$Tc-NC100692 scores ($r^2$=0.79, p=0.042). Correlation of borderline significance was seen between PD scores for the hands only and CT-SPECT of the hands ($r^2$=0.76, p=0.052).

Figure 5:
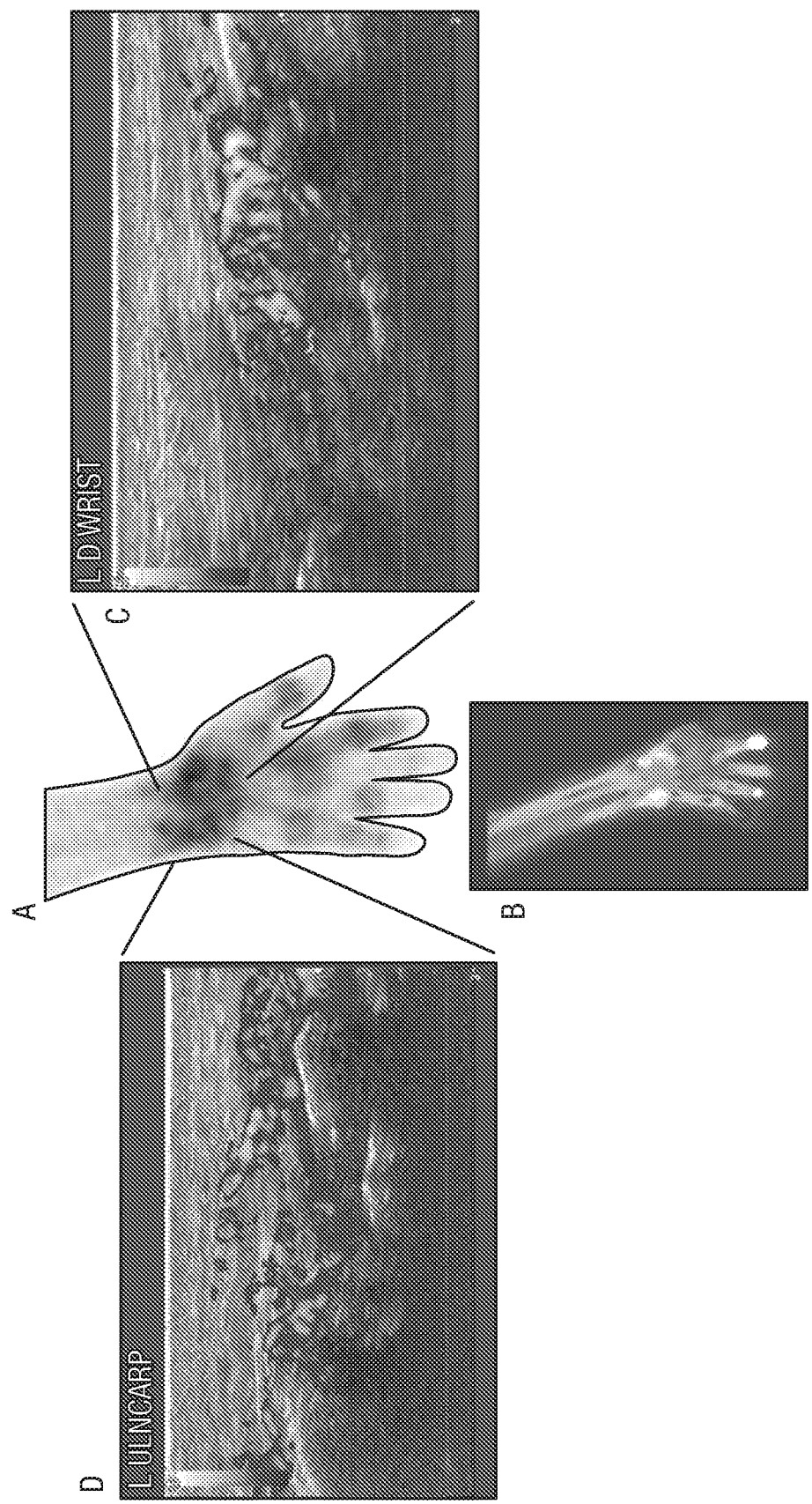
FIG. 5 shows planar (A) and SPECT/CT (B) $^{99m}$Tc-NC100692 of a hand and wrist with corresponding ultrasound with power Doppler images of wrist joint synovitis (C) and extensor carpi ulnaris tenosynovitis (D).

Analysis of the $^{99m}$Tc-NC100692 suggested that areas of uptake, as well as corresponding to areas of joint inflammation, also corresponded to areas of tenosynovitis as imaged on ultrasound (FIG. 5). Thus these results suggest that this technique could be used to quantify synovial inflammation in extra-articular areas as well as the joints.

Overall the procedure was well-tolerated. Static whole body, hand and foot images were similar at the two time points and hence the imaging protocol may be simplified for future studies.

Discussion

In this pilot proof-of principle study we have shown that $^{99m}$Tc-NC100692 uptake in the joints of patients with active RA is highly correlated with PDUS scores at the whole-body level. Our results validate the utility of the methods of the invention, and demonstrate that $^{99m}$Tc-NC100692 imaging may be a potential surrogate for PDUS imaging in patients with inflammatory arthritis.

There are currently no diagnostic tools capable of imaging synovitis at the whole body level that are suitable in clinical practice for the diagnosis or assessment of RA. Other technologies on the market such as US and MRI are expensive, enable imaging of relatively few joints and are complex to use requiring specialist training. $^{99m}$Tc-NC100692 imaging enables healthcare providers to offer a rapid whole body scan in 30 minutes. In addition, standard scanning equipment (gamma camera) may be used. Furthermore, $^{99m}$Tc-generation facilities are available in any nuclear medicine department and hence this is rapidly scalable as a technology.

Both scoring techniques employed in this study (fully quantified and a simple binary joint count) demonstrated strong correlation with PDUS and hence the potential for inter-observer variability is minimised.

RA has a very high economic burden on society with prevalence of 0.5-1% of the general population and up to 40% of patients are out of work 5 years after diagnosis.[27] It is estimated that the cost of treatment of RA is $19 billion and €42 billion per annum in US and Western Europe respectively.[28,29] In the UK there are around 20,000 new diagnoses per year with a total prevalence of about 400,000 in the adult population.[30,31]

Effective diagnosis and management of RA is dependent on reliable assessment of disease activity. This is of particular importance in ensuring early diagnosis where early treatment can result in improved long-term outcomes. In addition, in patients with established disease, accurate quantification of disease activity can help to stratify patients on expensive biologic therapies, for instance for patients in remission into groups in whom treatment can more safely be tapered and for those with active disease into those more likely to respond to a specific intervention. This has wide-ranging implications for patient outcomes and cost-effective use of expensive therapeutic resources (RA accounts for 3 of the 5 top-selling drugs worldwide with global revenues of $30 billion in 2013[32]). For example, in one exemplary clinical setting, about a third of RA patients are on biologic therapies costing about £15,000 per year per patient.

This study has demonstrated agreement and hence equivalence with US which has been shown to be of particular clinical value in the following patient groups:

Early Inflammatory Arthritis

In recent years it has become clear that there is a therapeutic 'window of opportunity' in early rheumatoid arthritis (ERA) during which aggressive treatment can significantly attenuate the long-term course of the disease.[33] As this period may be as short as 3 months, the challenge lies in early detection and diagnosis of the disease. Development of a prediction algorithm to identify patients at high risk of developing persistent erosive disease has met with considerable success.[34] This score forms the basis of current guidelines for the classification of RA.[35] However, there remain 25% of patients with an indeterminate score whose outcome will be unclear. There is therefore a pressing need for further refinement of these criteria in order to accurately determine risk in these patients.

PDUS has been shown to predict persistence of disease and development of joint erosions in prospective cohorts of patients with early arthritis and established RA.[36] PDUS score has also been shown to increase the sensitivity for prediction of progression to RA when combined with the clinical measures.[37-39] Again, this is time-consuming and the value of a technique of rapidly (and cheaply) assessing synovial inflammation in multiple joints is clear. Rapid risk stratification of such patients will reduce time to treatment with potentially enhanced outcomes and better stratify patients who do not need early disease-modifying therapy.

Remission and Low Disease Activity in RA

With the widespread use of biologic treatments for RA an increasing number of patients are achieving remission or low disease activity states. It is well-established that despite the lack of clinical synovitis joint damage can progress in some patients,[4] but in view of the uncertain risks and expense of long-term treatment with these drugs recent guidelines have recommended tapering of treatment in patients who are in disease remission.[40] A number of these patients will relapse[41] and it is therefore important to develop tools to determine in which patients it is safe to withdraw therapy. Increased PD signal is seen in a majority of RA patients in clinical remission[42], including in clinically uninflamed joints, is associated with risk of relapse in patients[43-45] and predicts flare when biologic therapy is tapered.[46] This risk is observed even if PD signal is only seen in a small number of joints: accurate outcome prediction therefore requires the systematic assessment of large numbers of joints which, again, is impractical in routine practice. More systematic assessment of these patients could enhance stratification of those suitable for drug tapering thus optimising the use of resources on expensive long-term therapies.

Assessment of Response to Biologic Therapies

Currently the gold standard for disease modification in RA is the assessment of radiological progression on plain X-Ray. In clinical practice progression is routinely evaluated over a period of 12 months because plain radiography has limited sensitivity to change over periods of less than one year. Although MRI and US have greater sensitivity for the detection of erosions they are expensive and time consuming especially if multiple joints are to be assessed. RA patients treated with biologics have been shown to have a reduction in PD signal as early as one month after treatment and this response can be predictive of clinical and radiological outcomes.[47-52] The methods of the invention, such as $^{99m}$Tc-NC100962-based nuclear imaging, therefore provide a powerful quantitative determinant of response to novel therapies such as biologics over short periods of time. Furthermore, PDUS activity has been shown to predict response to biologic agents prior to therapy[53,54]: this could help to determine which patients with active disease (who despite high DAS28 score may not always have clinically apparent inflammation) will respond to escalation of therapy. There are around 55 drugs (Pharmaceutical Research and Manufacturers of America, 2014 report) that are currently under active development for RA by numerous pharmaceutical companies. The methods of the invention such as $^{99m}$Tc-NC100692 imaging offer enormous potential for drug development enabling the companies to accelerate clinical trials, make early go/no-go decisions during clinical trials and to position their new drugs for the treatment of early RA disease.

Potential for Applications in Other Types of Inflammatory Arthritis

Although we have shown here that $^{99m}$Tc-NC100692 imaging has application in RA, the methods of the invention also have applications in other types of inflammatory arthropathies including, but not limited to, psoriatic arthritis, ankylosing spondylitis and other spondyloarthropathies (SpAs), and inflammatory arthritis associated with connective tissue diseases such as systemic lupus erythematosus. The methods of the invention also have application in imaging extra-articular sites of musculoskeletal inflammation that are associated with increased neovascularity on ultrasound such as (as we have shown) tendon sheaths and also entheses.

Enthesopathy (inflammation of tendon insertion into bone) is a common feature of SpAs diagnosis of which, when symptoms are mild, may be challenging. The presence of entheseal neovascularity as assessed by PDUS, has been shown to predict subsequent progression to an established spondyloarthropathy. Ultrasound scanning of multiple entheses is impractical for routine clinical use due to time constraints. The methods of the invention such as $^{99m}$Tc-NC100692 imaging have applications in imaging multiple areas of entheseal inflammation in a single acquisition. Another common feature of SpAs, particularly ankylosing spondylitis, is sacroiliitis. In conventional clinical practice inflammation at the sacroiliac joint can only be imaged by MRI. However, the methods of the invention, such as $^{99m}$Tc-NC100692, have application in imaging sacroiliitis as well as joint, entheseal and tendon inflammation in these patients, again in a single acquisition. No other imaging modality currently available has the potential to do this.

REFERENCES

1. Lee D M, Weinblatt M E. Rheumatoid arthritis. Lancet. 2001; 358(9285):903-11.
2. Wakefield R J, Green M J, Marzo-Ortega H, Conaghan P G, Gibbon W W, McGonagle D, et al. Should oligoarthritis be reclassified? Ultrasound reveals a high prevalence of subclinical disease. Ann Rheum Dis. 2004; 63(4):382-5.
3. Naredo E, Collado P, Cruz A, Palop M J, Cabero F, Richi P, et al. Longitudinal power Doppler ultrasonographic assessment of joint inflammatory activity in early rheumatoid arthritis: predictive value in disease activity and radiologic progression. Arthritis Rheum. 2007; 57(1):116-24.
4. Brown A K, Conaghan P G, Karim Z, Quinn M A, Ikeda K, Peterfy C G, et al. An explanation for the apparent dissociation between clinical remission and continued structural deterioration in rheumatoid arthritis. Arthritis Rheum. 2008; 58(10):2958-67.
5. Walther M, Harms H, Krenn V, Radke S, Faehndrich T P, Gohlke F. Correlation of power Doppler sonography with vascularity of the synovial tissue of the knee joint in patients with osteoarthritis and rheumatoid arthritis. Arthritis Rheum. 2001; 44(2):331-8.
6. Andersen M, Ellegaard K, Hebsgaard J B, Christensen R, Torp-Pedersen S, Kvist P H, et al. Ultrasound colour Doppler is associated with synovial pathology in biopsies from hand joints in rheumatoid arthritis patients: a cross-sectional study. Annals of the Rheumatic Diseases 73(4): 678-83, 2014.
7. Hirohata S, Sakakibara J. Angioneogenesis as a possible elusive triggering factor in rheumatoid arthritis. Lancet. 1999; 353(9161):1331.
8. Rooney M, Condell D, Quinlan W, Daly L, Whelan A, Feighery C, et al. Analysis of the histologic variation of synovitis in rheumatoid arthritis. Arthritis Rheum. 1988; 31(8):956-63.
9. Kennedy A, Ng C T, Biniecka M, Saber T, Taylor C, O'Sullivan J, et al. Angiogenesis and blood vessel stability in inflammatory arthritis. Arthritis Rheum. 2010; 62(3):711-21.
10. Eliceiri B P, Cheresh D A. The role of alphav integrins during angiogenesis: insights into potential mechanisms of action and clinical development. J Clin Invest. 1999; 103(9):1227-30.
11. Wilder R L. Integrin alpha V beta 3 as a target for treatment of rheumatoid arthritis and related rheumatic diseases. Ann Rheum Dis. 2002; 61 Suppl 2:ii96-ii9.
12. Gravallese E M, Manning C, Tsay A, Naito A, Pan C, Amento E, et al. Synovial tissue in rheumatoid arthritis is a source of osteoclast differentiation factor. Arthritis Rheum. 2000; 43(2):250-8.
13. Yanni G, Whelan A, Feighery C, Bresnihan B. Synovial tissue macrophages and joint erosion in rheumatoid arthritis. Ann Rheum Dis. 1994; 53(1):39-44.
14. Baeten D, Demetter P, Cuvelier C, Van den B F, Kruithof E, Van Damme N, et al. Comparative study of the synovial histology in rheumatoid arthritis, spondyloarthropathy, and osteoarthritis: influence of disease duration and activity. Ann Rheum Dis. 2000; 59(12):945-53.
15. Walsh D A, Wade M, Mapp P I, Blake D R. Focally regulated endothelial proliferation and cell death in human synovium. American Journal of Pathology. 1998; 152(3):691-702.
16. Gerlag D M, Borges E, Tak P P, Ellerby H M, Bredesen D E, Pasqualini R, et al. Suppression of murine collagen-induced arthritis by targeted apoptosis of synovial neo-vasculature. Arthritis Research. 2001; 3(6):357-61.
17. Koning G A, Schiffelers R M, Wauben M H, Kok R J, Mastrobattista E, Molema G, et al. Targeting of angiogenic endothelial cells at sites of inflammation by dexamethasone phosphate-containing RGD peptide liposomes inhibits experimental arthritis. Arthritis Rheum. 2006; 54(4):1198-208.
18. Storgard C M, Stupack D G, Jonczyk A, Goodman S L, Fox R I, Cheresh D A. Decreased angiogenesis and arthritic disease in rabbits treated with an alphavbeta3 antagonist. J Clin Invest. 1999; 103(1):47-54.
19. Bach-Gansmo T, Danielsson R, Saracco A, Wilczek B, Bogsrud T V, Fangberget A, et al. Integrin receptor imaging of breast cancer: a proof-of-concept study to evaluate 99mTc-NC100692. J Nucl Med. 2006; 47(9): 1434-9.
20. Kenny L M, Coombes R C, Oulie I, Contractor K B, Miller M, Spinks T J, et al. Phase I trial of the positron-emitting Arg-Gly-Asp (RGD) peptide radioligand 18F-AH111585 in breast cancer patients. J Nucl Med. 2008; 49(6):879-86.
21. Liu Z, Wang F. Development of RGD-based radiotracers for tumor imaging and therapy: translating from bench to bedside. [Review]. Current Molecular Medicine 13(10): 1487-505, 2013.
22. Zhu Z, Yin Y, Zheng K, Li F, Chen X, Zhang F, et al. Evaluation of synovial angiogenesis in patients with rheumatoid arthritis using (6)(8)Ga-PRGD2 PET/CT: a prospective proof-of-concept cohort study. Ann Rheum Dis. 2014; 73(6):1269-72.
23. GE Healthcare. NC100692 Investigators Brochure. 2010.
24. Dearling J L, Barnes J W, Panigrahy D, Zimmerman R E, Fahey F, Treves S T, et al. Specific uptake of 99mTc-NC100692, an alphavbeta3-targeted imaging probe, in subcutaneous and orthotopic tumors. Nucl Med Biol. 2013; 40(6):788-94.
25. Bach-Gansmo T, Bogsrud T V, Skretting A. Integrin scintimammography using a dedicated breast imaging, solid-state gamma-camera and (99m)Tc-labelled NC100692. Clin Physiol Funct Imaging. 2008; 28(4):235-9.
26. Axelsson R, Bach-Gansmo T, Castell-Conesa J, McParland B J. An open-label, multicenter, phase 2a study to assess the feasibility of imaging metastases in late-stage cancer patients with the alpha v beta 3-selective angiogenesis imaging agent 99mTc-NC100692. Acta Radiol. 2010; 51(1):40-6.
27. http://www.rheumatology.org.uk/includes/documents/cm+docs/2013/s/simple_tasks_fast_facts_pdf.pdf [accessed April 2015]
28. Birnbaum H, Pike C, Kaufman R, Marynchenko M, Kidolezi Y, Cifaldi M. Societal cost of rheumatoid arthritis patients in the US. Curr Med Res Opin. 2010; 26(1): 77-90.
29. Lundkvist J, Kastang F, Kobelt G. The burden of rheumatoid arthritis and access to treatment: health burden and costs. Eur J Health Econ. 2008; 8 Suppl 2:S49-S60.
30. Wiles N, Symmons D P, Harrison B, Barrett E, Barrett J H, Scott D G, et al. Estimating the incidence of rheumatoid arthritis: trying to hit a moving target? Arthritis Rheum. 1999; 42(7):1339-46.
31. Symmons D, Turner G, Webb R, Asten P, Barrett E, Lunt M, et al. The prevalence of rheumatoid arthritis in the United Kingdom: new estimates for a new century. Rheumatology (Oxford). 2002; 41(7):793-800.
32. www.firstwordpharma.com 2015 [accessed April 2015].
33. Mottonen T, Hannonen P, Korpela M, Nissila M, Kautiainen H, Ilonen J, et al. Delay to institution of therapy and induction of remission using single-drug or combination-disease-modifying antirheumatic drug therapy in early rheumatoid arthritis. Arthritis Rheum. 2002; 46(4):894-8.
34. A H vdH-vM, Detert J, le C S, Filer A, Bastian H, Burmester G R, et al. Validation of a prediction rule for disease outcome in patients with recent-onset undifferentiated arthritis: moving toward individualized treatment decision-making. Arthritis Rheum. 2008; 58(8):2241-7.
35. Aletaha D, Neogi T, Silman A J, Funovits J, Felson D T, Bingham C O, III, et al. 2010 Rheumatoid arthritis classification criteria: an American College of Rheumatology/European League Against Rheumatism collaborative initiative. Arthritis Rheum. 2010; 62(9):2569-81.
36. Funck-Brentano T, Gandjbakhch F, Etchepare F, Jousse-Joulin S, Miguel A, Cyteval C, et al. Prediction of radiographic damage in early arthritis by sonographic erosions and power Doppler signal: a longitudinal observational study. Arthritis care & research 65(6):896-902, 2013.
37. Freeston J E, Wakefield R J, Conaghan P G, Hensor E M, Stewart S P, Emery P. A diagnostic algorithm for persistence of very early inflammatory arthritis: the utility of power Doppler ultrasound when added to conventional assessment tools. [Erratum appears in Ann Rheum Dis. 2011 August; 70(8):1519]. Annals of the Rheumatic Diseases 69(2):417-9, 2010.
38. Filer A, de P P, Allen G, Nightingale P, Jordan A, Jobanputra P, et al. Utility of ultrasound joint counts in the prediction of rheumatoid arthritis in patients with very early synovitis. Annals of the Rheumatic Diseases 70(3): 500-7, 2011.
39. Nakagomi D, Ikeda K, Okubo A, Iwamoto T, Sanayama Y, Takahashi K, et al. Ultrasound can improve the accuracy of the 2010 American College of Rheumatology/European League against rheumatism classification criteria for rheumatoid arthritis to predict the requirement for methotrexate treatment. Arthritis & Rheumatism 65(4): 890-8, 2013.
40. Excellence NIfHaC. Rheumatoid arthritis: national clinical guideline for management and treatment in adults. www nice org uk [Internet]. 2009.
41. O'Mahony R, Richards A, Deighton C, Scott D. Withdrawal of disease-modifying antirheumatic drugs in patients with rheumatoid arthritis: a systematic review and meta-analysis. Ann Rheum Dis. 2010; 69(10):1823-6.
42. Kawashiri S Y, Suzuki T, Nakashima Y, Horai Y, Okada A, Iwamoto N, et al. Ultrasonographic examination of rheumatoid arthritis patients who are free of physical synovitis: power Doppler subclinical synovitis is associated with bone erosion. Rheumatology 53(3):562-9, 2014.
43. Saleem B, Keen H, Goeb V, Parmar R, Nizam S, Hensor E M, et al. Patients with RA in remission on TNF blockers: when and in whom can TNF blocker therapy be stopped? Ann Rheum Dis. 2010; 69(9):1636-42.
44. Scire C A, Montecucco C, Codullo V, Epis O, Todoerti M, Caporali R. Ultrasonographic evaluation of joint involvement in early rheumatoid arthritis in clinical remission: power Doppler signal predicts short-term relapse. Rheumatology 48(9):1092-7, 2009.
45. Peluso G, Michelutti A, Bosello S, Gremese E, Tolusso B, Ferraccioli G. Clinical and ultrasonographic remission determines different chances of relapse in early and long standing rheumatoid arthritis. Annals of the Rheumatic Diseases 70(1):172-5, 2011.
46. Iwamoto T, Ikeda K, Hosokawa J, Yamagata M, Tanaka S, Norimoto A, et al. Prediction of relapse after discontinuation of biologic agents by ultrasonographic assessment in patients with rheumatoid arthritis in clinical remission: high predictive values of total gray-scale and power Doppler scores that represent residual synovial inflammation before discontinuation. Arthritis care & research 66(10):1576-81, 2014.
47. Taylor P C, Steuer A, Gruber J, Cosgrove D O, Blomley M J, Marsters P A, et al. Comparison of ultrasonographic assessment of synovitis and joint vascularity with radiographic evaluation in a randomized, placebo-controlled study of infliximab therapy in early rheumatoid arthritis. Arthritis Rheum. 2004; 50(4):1107-16.
48. Taylor P C, Steuer A, Gruber J, McClinton C, Cosgrove D O, Blomley M J, et al. Ultrasonographic and radiographic results from a two-year controlled trial of immediate or one-year-delayed addition of infliximab to ongoing methotrexate therapy in patients with erosive early rheumatoid arthritis. Arthritis & Rheumatism 54(1):47-53, 2006.
49. Hama M, Uehara T, Takase K, Ihata A, Ueda A, Takeno M, et al. Power Doppler ultrasonography is useful for assessing disease activity and predicting joint destruction in rheumatoid arthritis patients receiving tocilizumab—preliminary data. Rheumatology International 32(5): 1327-33, 2012.
50. Kume K, Amano K, Yamada S, Hatta K, Kuwaba N, Ohta H. Very early improvements in the wrist and hand assessed by power Doppler sonography predicting later favorable responses in tocilizumab-treated patients with rheumatoid arthritis. Arthritis care & research 63(10): 1477-81, 2011.
51. Fukae J, Isobe M, Kitano A, Henmi M, Sakamoto F, Narita A, et al. Radiographic prognosis of finger joint damage predicted by early alteration in synovial vascularity in patients with rheumatoid arthritis: Potential utility of power doppler sonography in clinical practice. Arthritis care & research 63(9):1247-53, 2011.
52. Hammer H B, Kvien T K. Comparisons of 7- to 78-joint ultrasonography scores: all different joint combinations show equal response to adalimumab treatment in patients with rheumatoid arthritis. Arthritis Research & Therapy 13(3):R78, 2011.
53. Ellegaard K, Christensen R, Torp-Pedersen S, Terslev L, Holm C C, Konig M J, et al. Ultrasound Doppler measurements predict success of treatment with anti-TNF-α drug in patients with rheumatoid arthritis: a prospective cohort study. Rheumatology 50(3):506-12, 2011.
54. Reiche B E, Ohrndorf S, Feist E, Messerschmidt J, Burmester G R, Backhaus M. Usefulness of power Doppler ultrasound for prediction of re-therapy with rituximab in rheumatoid arthritis: a prospective study of longstanding rheumatoid arthritis patients. Arthritis care & research 66(2):204-16, 2014.

The invention claimed is:

1. A method of imaging arthritis in a subject, comprising administering to the subject a tracer which comprises a peptide conjugated to a radionuclide, and imaging the subject by 2D nuclear imaging or by 3D detection of single-photon emission events, wherein said radionuclide is $^{99m}Tc$ and said peptide is a compound having a formula:

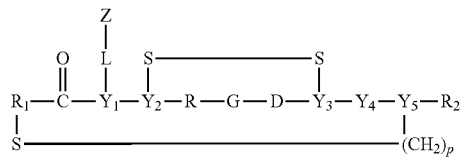

[Formula (II)]

wherein:

R is arginine or N-methyl arginine;

G is glycine;

D is aspartic acid;

$Y_1$ is an amino acid residue selected from the group consisting of: aspartic acid, glutamic acid, asparagine, glutamine, lysine and arginine, wherein the side-chain of $Y_1$ is bonded via a heteroatom in the side-chain to the moiety -L-Z;

—$Y_2$—S— and —$Y_3$—S— each independently are an amino acid residue which forms a disulphide bond —$Y_2$—S—S—$Y_3$—;

$Y_4$ is an amino acid residue selected from the group consisting of: valine, leucine, isoleucine, methionine, phenylalanine, tyrosine and tryptophan;

—$Y_5$—$(CH_2)_n$—S— is a sulphur-containing amino acid residue; wherein p is 1 or 2;

$R_1$ is —$(CH_4)_q$—$(Ar)_r$—$(CH_2)_s$—, wherein q and s are each independently 0 or an integer, wherein q+s is an integer from 1 to 8, and wherein r is 0 or 1; and wherein Ar is a $C_6$ arylene group;

$R_2$ is absent or is -Het-$((CH_2)_n$Het$)_m R^b$Het$R^a$;

n is 1 or 2;

m is an integer from 1 to 6;

each Het is independently —O— or —$NR^a$—;

$R^b$ is absent or is $C_1$ to $C_6$ alkylene which is optionally substituted by from 1 to 3 oxo groups and/or is interrupted by from 1 to 3 groups selected from —O— and —C(O)—;

each $R^a$ is independently selected from H and $C_1$ to $C_2$ alkyl;

L is —C(O)—($C_1$-$C_6$ alkylene)-C(O)—; wherein the alkylene group of L is optionally interrupted by —O— and/or wherein the alkylene group of L is unsubstituted or substituted by 1 or 2 substituents selected from the group consisting of: —OH, $C_1$ to $C_2$ alkoxy and $C_1$ to $C_2$ alkyl;

Z is a moiety of Formula (III)

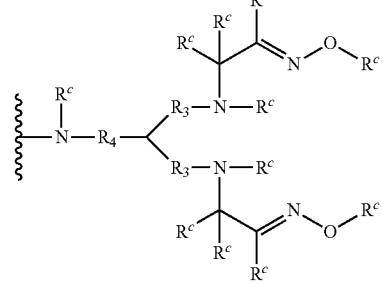

[Formula (III)]

wherein:

each group $R^c$ is independently H or $C_1$ to $C_2$ alkyl;

each group $R_3$ is independently $C_1$ to $C_3$ alkylene;

$R_4$ is $C_1$ to $C_4$ alkylene; and each alkyl group and/or each alkylene group is unsubstituted or is substituted with 1 substituent selected from —OH, —$N(R^a)_2$, $C_1$ to $C_2$ alkyl, and $C_1$ to $C_2$ alkoxy.

2. A method according to claim 1 wherein imaging the subject comprises imaging the subject by 2D scintigraphy using a gamma camera or by single photon emission computational tomography (SPECT).

3. A method according to claim 1 wherein q+s is an integer from 1 to 3.

4. A method according to claim 1, further wherein $Y_1$ is lysine;

—$Y_2$—S— and —$Y_3$—S— each independently represent cysteine;

$Y_4$ is an amino acid residue selected from phenylalanine and tyrosine;

$R_2$ is —NH—$((CH_2)_2$Het$)_m R^b$Het$R^a$;

m is an integer from 3 to 6;

Het is —O— or —$NR^a$—;

$R^a$ is H;

$R^b$ is —C(O)—$CH_2$—O—$CH_2$—C(O)—; and

L is —C(O)—($C_1$-$C_6$ alkylene)-C(O)—; wherein the alkylene group of L is unsubstituted.

5. A method according to claim 1 wherein Z is a moiety of Formula (IV)

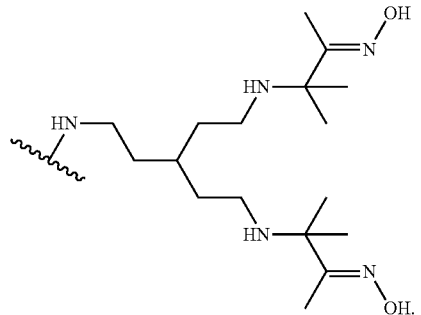

[Formula (IV)]

6. A method according to claim 5, further wherein:

$Y_4$ is phenylalanine; and

L is —C(O)—($C_2$-$C_4$ alkylene)-C(O)—; wherein the alkylene group of L is unsubstituted.

7. A method according to claim 1 wherein the peptide conjugated to the radionuclide is of Formula (VIa)

[Formula (VIa)]
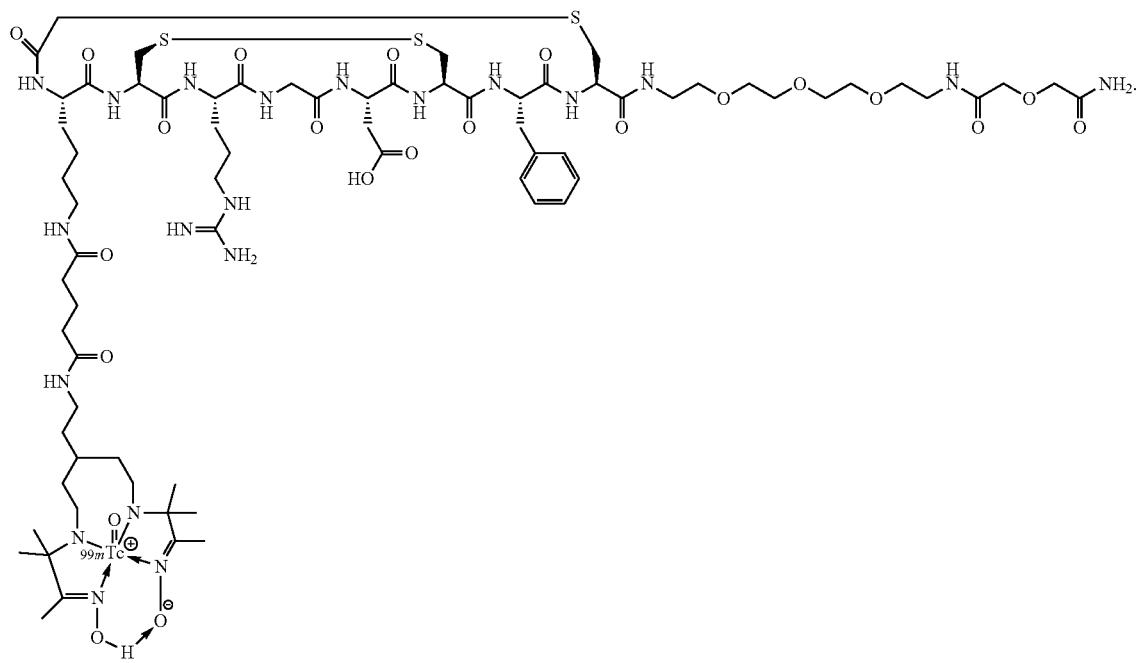
* * * * *

UNITED STATES PATENT AND TRADEMARK OFFICE
CERTIFICATE OF CORRECTION

PATENT NO. : 10,729,793 B2
APPLICATION NO. : 15/739220
DATED : August 4, 2020
INVENTOR(S) : Toby Garrood Page 1 of 1

It is certified that error appears in the above-identified patent and that said Letters Patent is hereby corrected as shown below:

In the Claims

Column 37, Claim 1, Line 44 – please replace "$(CH_4)_q$" with ---$(CH_2)_q$---.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*